(12) United States Patent
Khopade et al.

(10) Patent No.: US 8,586,062 B2
(45) Date of Patent: Nov. 19, 2013

(54) NANODISPERSION

(75) Inventors: Ajay Jaysingh Khopade, Baroda (IN); Subhas Balaram Bhowmick, Baroda (IN); Natarajan Arulsudar, Baroda (IN)

(73) Assignee: Sun Pharma Advanced Research Company Ltd., Mumbai (IN)

( * ) Notice: Subject to any disclaimer, the term of this patent is extended or adjusted under 35 U.S.C. 154(b) by 311 days.

(21) Appl. No.: 12/810,428

(22) PCT Filed: Dec. 23, 2008

(86) PCT No.: PCT/IN2008/000857
§ 371 (c)(1),
(2), (4) Date: Aug. 6, 2010

(87) PCT Pub. No.: WO2009/087678
PCT Pub. Date: Jul. 16, 2009

(65) Prior Publication Data
US 2010/0297244 A1  Nov. 25, 2010

(30) Foreign Application Priority Data
Dec. 24, 2007 (IN) .................. 2527/MUM/2007

(51) Int. Cl.
*A61K 9/00* (2006.01)
*A61K 9/14* (2006.01)

(52) U.S. Cl.
USPC ........................ 424/400; 424/489

(58) Field of Classification Search
None
See application file for complete search history.

(56) References Cited

U.S. PATENT DOCUMENTS

| | | | |
|---|---|---|---|
| 5,399,363 A * | 3/1995 | Liversidge et al. | 424/490 |
| 6,017,948 A | 1/2000 | Rubinfeld et al. | |
| 6,046,230 A | 4/2000 | Chung et al. | |
| 6,294,192 B1 * | 9/2001 | Patel et al. | 424/451 |
| 6,365,191 B1 | 4/2002 | Burman et al. | |
| 6,537,579 B1 | 3/2003 | Desai et al. | |
| 6,753,006 B1 | 6/2004 | Desai et al. | |
| 2002/0058060 A1 | 5/2002 | Kan et al. | |
| 2002/0192280 A1 * | 12/2002 | Hunter et al. | 424/465 |
| 2003/0109575 A1 * | 6/2003 | Lambert et al. | 514/458 |
| 2004/0092428 A1 * | 5/2004 | Chen et al. | 514/2 |
| 2004/0234597 A1 * | 11/2004 | Shefer et al. | 424/468 |
| 2005/0238673 A1 * | 10/2005 | Augustine et al. | 424/400 |
| 2005/0288521 A1 * | 12/2005 | Naidu et al. | 549/510 |
| 2006/0024374 A1 | 2/2006 | Gasco et al. | |
| 2006/0188566 A1 | 8/2006 | Liversidge et al. | |
| 2009/0163574 A1 * | 6/2009 | Kim et al. | 514/449 |
| 2010/0068251 A1 * | 3/2010 | Ali et al. | 424/450 |

FOREIGN PATENT DOCUMENTS

| | | |
|---|---|---|
| WO | 01/21174 A1 | 3/2001 |
| WO | 03/077882 A2 | 9/2003 |
| WO | 2004/039351 A2 | 5/2004 |
| WO | 2006/133510 A1 | 12/2006 |
| WO | 2007/069272 A2 | 6/2007 |

OTHER PUBLICATIONS

Lacko, A.G., et al., "High Density Lipoprotein Complexes as Delivery Vehicles for Anticancer Drugs", 2002, Anticancer Research, pp. 2045-2049.*
International Search Report of PCT/IN2008/000857, Mailing Date of Jun. 26, 2009.

* cited by examiner

*Primary Examiner* — Michael G Hartley
*Assistant Examiner* — Lance Rider
(74) *Attorney, Agent, or Firm* — Sughrue Mion, PLLC

(57) ABSTRACT

The present invention provides a nanodispersion comprising nanoparticles having a mean size less than 300 nm dispersed in a vehicle comprising a water miscible solvent and water, said nanoparticles comprising one or more taxane derivative, a polymer and a surfactant comprising a mixture of fatty acids or its salts and sterol or its derivatives or its salts.

10 Claims, 4 Drawing Sheets

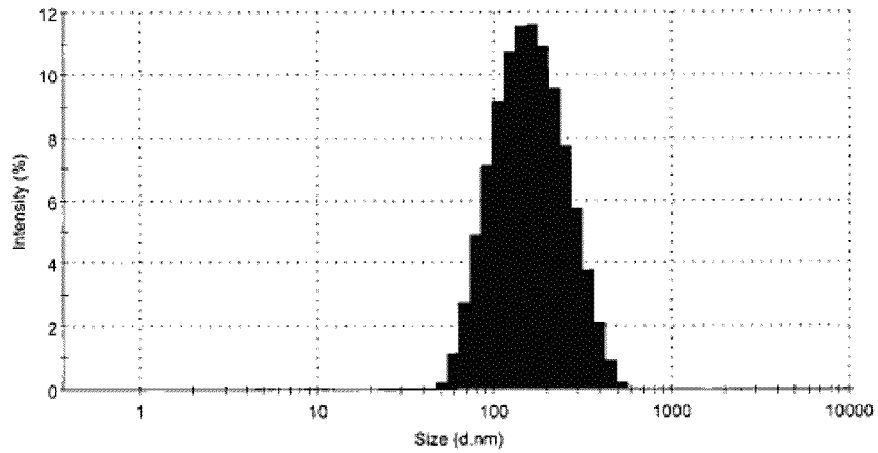
Figure 4 (a): Histogram showing particle size distribution of the nanodispersion of Example 9 at initial time
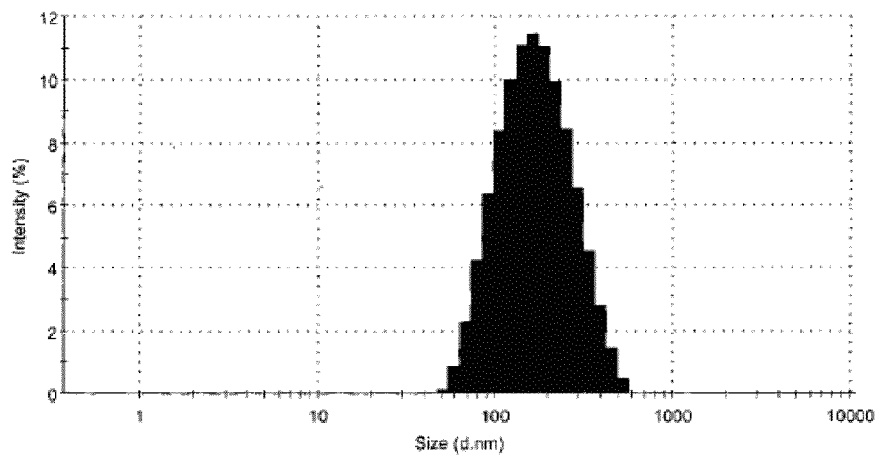
figure 4 (b): The histogram showing the particle size distribution of the nanodispersion of paclitaxel Eample 9 when stored at room temperature for 24 hours

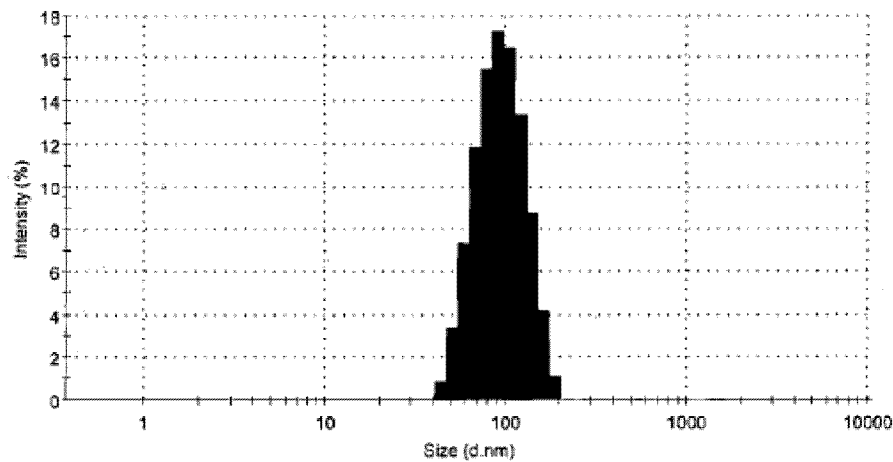
Figure 5 (a): indicates a histogram showing particle size distribution of the nanodispersion of docetaxel of Example 24 D at initial time
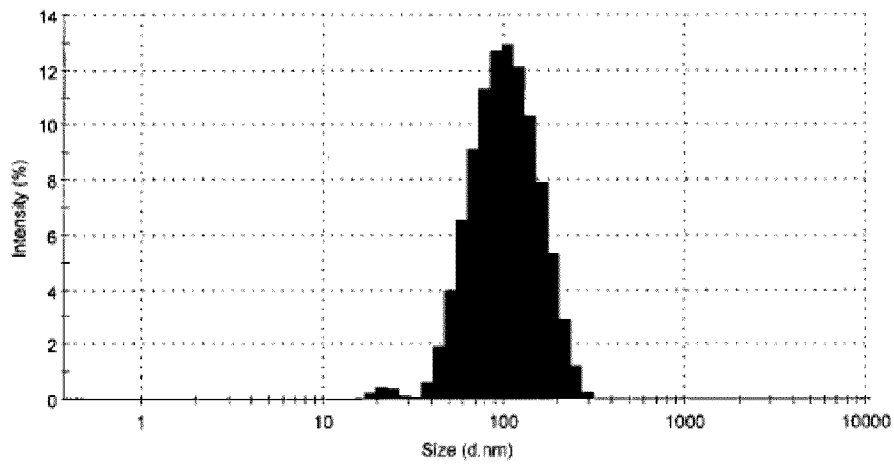
Figure 5 (b): The histogram showing the particle size distribution of the nanodispersion of docetaxel of Example 24 D when stored at room temperature for 8 hours.

NANODISPERSION

The present invention relates to a 'nanodispersion' of a taxane derivative and process for its preparation.

BACKGROUND OF THE INVENTION

There are number of pharmaceutical drugs that are poorly soluble or insoluble in aqueous solutions. Such drugs provide challenges in terms of having poor oral bioavailability or in terms of formulating them for drug delivery especially through the intravenous route. If a drug is intravenously administered, particles must be small enough to safely pass through capillaries without causing emboli. For intravenous administration, it is recognized as safe to administer drugs in the form of solution, emulsion, liposomes, nanodispersions and the like. Another requirement that should be met while formulating a drug delivery system especially for hydrophobic drugs is that the formulation should be physically stable with no substantial aggregation or crystallization of the drug or change in appearance of the formulation on storage at room temperature for desired period of time.

An example of a poorly soluble drug includes taxane derivatives which are well known for their anticancer activity. A taxane derivative or a taxoid is a complex diterpenoid natural product derived principally from the bark of the Western Yew, *Taxus brevifolia* and essentially has a taxane skeleton. Taxanes have been used to produce various chemotherapeutic drugs. Currently two taxane derivatives paclitaxel and docetaxel are available commercially as potent anti-tumor agents.

The taxane derivatives exhibit very poor solubility in water and in most pharmaceutically acceptable solvents thus limiting their administration to patients. Due to this unfavorable intrinsic property, TAXOL injection, the commercially marketed paclitaxel injection is formulated as a non-aqueous solution in Cremophor™ EL (a polyethoxylated castor oil) and dehydrated alcohol. However, use of solubilizer like Cremophor™ EL in large amounts lead to various adverse effects such as serious or fatal hypersensitive and hypertensive reactions, brady arrhythmia, anemia, neutropenia and/or peripheral neuropathy. Therefore all patients receiving paclitaxel are premedicated with steroids, antihistamines and H2 receptor antagonists and then paclitaxel is only infused very slowly over a period of at least 3 hours or more.

In view of these problems associated with Taxol formulations, researchers have tried to prepare taxol formulations without using Cremophor EL.

U.S. Pat. No. 6,537,579 describes compositions of substantially water insoluble pharmacologically active agents such as paclitaxel, in which the pharmacologically active agent exists in the form of suspended particles coated with protein (which acts as a stabilizing agent). In particular, protein and pharmacologically active agent in a biocompatible dispersing medium are subjected to high shear, in the absence of any conventional surfactants, and also in the absence of any polymeric core material for the particles. The procedure yields particles with a diameter of less than about 1 micron. The particulate system produced according to the invention can be converted into a redispersible dry powder comprising nanoparticles of water-insoluble drug coated with a protein, and free protein to which molecules of the pharmacological agent are bound.

U.S. Pat. No. 6,017,948 relates to a composition comprising paclitaxel in the form of a solution of paclitaxel in a pharmaceutically acceptable, water-miscible, non-aqueous solvent (like N-methylpyrrolidone) and further comprising a pharmaceutically acceptable solubilizer (such as triacetin), with the provision that polyethoxylated castor oil (Cremophor) is excluded from the composition. In preferred embodiments, a large amount of solvent i.e. 4000 mg of NMP (example 1) or combination of 2000 mg of NMP and 2000 mg of ethanol (example2) were used to solubilize 10 mg of paclitaxel under moderate agitation. If therapeutically effective amount of drug is delivered through such compositions, it will be associated with entry of excessive amounts of ethanol, non-aqueous solvents or solubilizers in the body.

U.S. Pat. No. 6,046,230 relates to a stable injection formulation containing paclitaxel and two solubilizers—oxyethylene sorbitol oleate and (oxyethylene glycol)$_{15\text{-}20}$ fatty acid monoester along with additional components such as povidone and polyethylene glycol. The main solubilizer used in the formulation polyethoxylated sorbitol oleic polyester which is an ethylene oxide addition product of palm olein-derived oleic acid has an inherent property of getting solidified at temperatures below 10° C., making it unsuitable for solubilizing paclitaxel when used alone. However when combined with an auxillary solubilizer polyethylene glycol mono fatty acid ester, the two solubilizers together exhibit good solubility in water and in anhydrous alcohol and they stay in fluid phase even at low temperatures. So, use of the two solubilizers together is mandatory. Also it is an essential criterion that HLB value of the solubilizers which meet the desired characteristics should be as high as 15 but not less than 13. The resulting formulation is a solution.

PCT Application no. WO 2006/133510 discloses a liquid pharmaceutical formulation for parenteral administration comprising docetaxel or a pharmaceutically acceptable salt thereof; one or more glycols and a pharmaceutically acceptable non-aqueous solvent system, wherein the formulation has a pH meter reading in the range of from 2.5 to 7.0. The embodiments of the invention involve use of very high amount of surfactants (about 25% v/v of polysorbate 80 or 30% v/v of Cremophor) which in turn can lead to toxic side effects. The application does not disclose the efficacy and toxicity profile of the formulations. Further the formulation disclosed by the '510 application is a solution of drug in a non-aqueous solvent system which on admixture with an infusion diluent (0.9% NaCl or 5% Dextrose solution) produces an infusion solution. A novel drug delivery system or nanodispersion is not formed anywhere in the process. Also the stability of the formulation solutions after diluting with infusion diluent is of very short period of about 4 to 6 hours which can limit its administration efficiency.

US2002/0058060 (hereinafter referred to as patent application '060) discloses liposomes containing hydrophobic substances and two phospholipids with different phase transition temperatures and liposome forming materials like cholesterol and hydrophilic polymer modified lipids. The ratio of the drug to the phospholipids and the liposome forming materials is varied to get different liposomal formulations. The patent application '060 indicates several attempts to formulate liposomes of taxanes which have elevated drug:lipid ratio, by using two specified class of phospholipids, so that total amount of lipid used is reduced, as injection of excessive amount of lipids in the body leads to certain extent of toxicity.

Thus it is evident from the prior art that the major problem associated with formulating a taxane composition is hydrophobicity of taxanes, which
  (a) makes it difficult to formulate a composition which contains solubilized form of the drug and which is stable, without any substantial aggregation or crystallization of the drug or change in appearance of the formulation till a desired period of time (b) necessitates the use of large amount of solubilizers, phospholipids and surfactants.

Also, toxicity studies of TAXOL (marketed solution of paclitaxel in Cremophor and Alcohol) shows a $LD_{50}$ value of 7.5-12.0 mg/kg as disclosed in U.S. Pat. No. 6,753,006 which is low, indicating that the drug administered in the form of solution has very low therapeutic index and even a moderate dose may show serious side effects and toxic reactions.

Thus there exists a need for an injectable formulation of a taxane derivative which
(a) avoids the use of large amount of excipients,
(b) avoids the use of Cremophor,
(c) delivers the drug through a novel delivery system, which shows increased $LD_{50}$ value, minimizing the toxic side effects associated with the administration of the drug in solution form and
(e) overcomes the limitations of the drug associated with its hydrophobic nature and is stable with no substantial aggregation or crystallization of the drug or change in appearance of the formulation, for the desired period of time during administration and during storage.

We have developed a nanodispersion comprising nanoparticles having a mean size less than 300 nm dispersed in a vehicle comprising a water miscible solvent and water, said nanoparticles comprising a taxane derivative, a polymer and very low amount of surfactants. The present invention provides a formulation which avoids the use of Cremophor, involves the use of much reduced amounts of additives (phospholipids) and delivers the drug in the form of nanoparticles, thus minimizing the toxic reactions and side effects associated with the administration of the drug. The $LD_{50}$ value observed for formulations of the present invention is 342.5 mg/kg which is much greater than the $LD_{50}$ value of 7.5-12.0 mg/kg of marketed TAXOL® solution as disclosed in U.S. Pat. No. 6,753,006. Also the formulation of the present invention is stable, with no substantial aggregation or crystallization of the drug or change in appearance of the formulation, for the desired period of time during administration and during storage.

OBJECTS OF THE INVENTION

It is the object of the present invention to provide a nanodispersion of a taxane derivative that is stable for the desired period of time before and during administration by parenteral route.

It is another object of the present invention to provide a nanodispersion that shows no sign of aggregation or change in appearance on storage to more than 4 hours at room temperature.

It is a further object of the present invention to provide a pre-concentrate of taxane derivative which is stable chemically and shows no sign of aggregation or change in appearance on storage for at least 3 months at room temperature and which upon dilution with an aqueous liquid vehicle gives a stable nanodispersion.

It is yet another object of the present invention to provide a kit having two containers, the first container comprising the pre-concentrate of the taxane derivative in a water miscible solvent and a second container comprising an aqueous liquid vehicle, such that on addition of contents of second container to the contents of the first container or vice versa, a stable nanodispersion is formed that is suitable for intravenous administration with the application of only mild agitation or shaking.

It is yet another object of the present invention to provide a kit having more than two containers for example, two containers, the first container comprising a lyophilized form of the nanodispersion and a second container comprising an aqueous liquid vehicle such that on addition of contents of second container to the contents of the first container or vice versa, a stable nanodispersion is formed that is suitable for intravenous administration with the application of only mild agitation or shaking.

It is a further object of the present invention to provide a method of treatment cancers said method comprising administering the nanodispersion compositions to patients in need thereof.

SUMMARY OF THE INVENTION

The present invention provides a nanodispersion comprising nanoparticles having a mean particle size less than 300 nm dispersed in a vehicle comprising a water miscible solvent and water, said nanoparticles comprising one or more taxane derivative, a polymer and a surfactant comprising a mixture of fatty acids or its salts and a sterol or its derivatives or its salts.

The present invention also provides a solution comprising one or more taxane derivative, a polymer and a surfactant comprising a mixture of fatty acids or its salts and sterol or its derivatives or its salts in a water miscible solvent, which upon dilution with an aqueous liquid vehicle gives nanodispersion.

The present invention also provides nanoparticles having a mean particle size less than 300 nms comprising one or more taxane derivative, surfactant comprising a mixture of sterol or its derivatives or its salts and fatty acid or its salts and a polymer.

BRIEF DESCRIPTION OF FIGURES

FIG. 4: The FIG. 4 (a) indicates a histogram showing particle size distribution of the nanodispersion of Example 9 at initial time and FIG. 4 (b) indicates the histogram showing the particle size distribution of the nanodispersion of paclitaxel example 9 when stored at room temperature for 24 hours.

FIG. 5: The FIG. 5 (a) indicates a histogram showing particle size distribution of the nanodispersion of Example 24D at initial time and FIG. 5 (b) indicates the histogram showing the particle size distribution of the nanodispersion of docetaxel of example 24D when stored at room temperature for 8 hours.

DETAILED DESCRIPTION OF THE INVENTION

Figure 1:
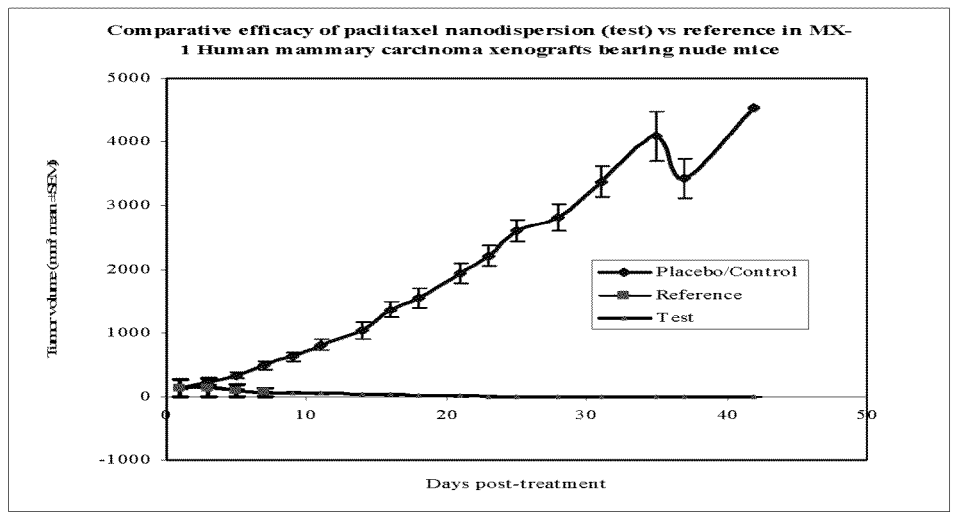
FIG. 1: It represents a comparative account of change in tumor volume with time (in days) of human breast tumor xenograft (MX-1) implanted in Balb/c female nude mice for control sample, reference sample (ABRAXANE®) and test sample (Composition of example 12a of the present invention) as per the study detailed in Example 27.

The present invention provides a nanodispersion comprising nanoparticles having a mean particle size less than 300 nm dispersed in an aqueous vehicle comprising a water miscible solvent and water, said nanoparticles comprising a taxane derivative, a polymer and a surfactant comprising a mixture of fatty acids or its salts and sterol or its derivatives or its salts.

The present invention also provides a solution comprising a taxane derivative, a polymer and a surfactant comprising a mixture of fatty acids or its salts and sterol or its derivatives or its salts in a water miscible solvent, which upon dilution with an aqueous vehicle gives nanodispersion.

The present invention is also related to nanoparticles having a mean particle size less than 300 nms comprising taxane derivative, surfactant comprising a mixture of sterol or its derivatives or its salts and fatty acid or it salts and a polymer. The nanodispersion of the present invention is devoid of toxic excipients like Cremophor and involves the use of much reduced amounts of additives (like surfactants and phospholipids) required for formulating a stable nanodispersion of taxane derivative, thus minimizing the associated toxic reactions.

Nanoparticles or nanosized particles in themselves afford many advantages in terms of efficient drug delivery. It has been realized that either incorporation of a drug into a delivery vehicle or attachment of the drug to the vehicle can afford many advantages in comparison to the administration of the drug in its free form. Incorporation of drug in vehicle can affect tissue specific distribution, in particular preferential accumulation in a certain tissue of interest or at a disease site, targeting of drug to a particular cell type, decrease of interaction with blood components, enhanced protection of the drug from premature degradation and increase in circulation time. Nanoparticle is one such important drug delivery vehicle. Nanoparticles have engineered specificity, allowing them to deliver a higher concentration of pharmaceutical agent to a desired location or target site of action (Kayser et al, Current Pharmaceutical Biotechnology, 2005, 6, page number 3-5). Targeted drug delivery is important in many applications, especially when toxicity of the drug, if delivered systemically, is an issue. Targeted drug delivery may help eliminate or at least minimize toxic side effects and lower the required dosage amounts, among other beneficial features. There are different approaches to target drugs to the site of action. A very simple, but in its applicability limited approach is the direct injection at the target site, e.g. injection into tumor tissue. Another approach is to use specific carrier systems for different administration routes (e.g. transferosomes for topical delivery), microspheres or nanoparticles for oral and parenteral administration. Out of the parenteral routes, the intravenous injection is most frequently used. Upon i.v. administration, particles are recognized by liver and spleen macrophages and preferentially they are taken up by the liver macrophages. This effect can be exploited to target drug-loaded carriers to liver and spleen or generally to macrophages to treat infections of the MPS (mononuclear phagocytic system) or RES (Reticulo endothelial system) and this targeting phenomenon is often called "passive targeting"). Escaping the MPS/RES recognition is possible by modifying the surface of the carriers with polyethylene glycol (PEG) moieties or PEG chain containing polymer such as Poloxamine 908. This increases the period of circulation of the carrier in the blood-stream upon intravenous injection. The normal as well as long circulating carriers can be equipped with a targeting moiety (lectins or monoclonal antibodies or sugars like mannose/galactose etc.) generally called as a ligand. These ligands direct the drug containing carriers to the desired target cells carrying the appropriate receptors for the ligands. This site specific delivery achieved by using a targeting ligand involves an active process; therefore it is also called as "active targeting". Nanoparticles having specific size, can passively target solid tumors through a phenomenon which exploits the characteristic features of tumor biology. Tumor tissues have leaky blood vessels, enhanced permeability and poor lymphatic drainage. In contrast, vascular endothelial cells in normal tissue have a lower permeability for nanoparticles compared to tumor tissues. This allows nanocarriers to accumulate in the tumor. The effect is known as Enhanced Permeability and Retention Effect or EPR Effect (Nanoparticle Technology for drug delivery, edited by Ram B. Gupta and Uday B. Kompella, published by Taylor and Francis, 2005, page 539). Also, nanoparticles less than 200 nm more effectively evade the reticuloendothelial system and remain in circulation for long time (Naoparticle Technology for drug delivery, edited by Ram B. Gupta and Uday B. Kompella, published by Taylor and Francis, 2005, page 540).

The term nanoparticle as used herein means any particle having controlled dimensions of the order of nanometers. The nanoparticles as claimed in the present invention can be a polymeric nanoparticle (matrix of polymer entrapping the drug) and/or a polymeric nanovesicle (polymer stabilized nano sized vesicle encapsulating the drug.) and/or a polymeric nanocapsule (polymeric membrane surrounding drug in core) and/or nano sized particles of the drug stabilized by surfactants, and the like having mean size less than 300 nm. The particle size of the nanoparticles is determined using conventional methods of measuring and expressing particle size like Malvern particle size analysis, sieving, light scattering optical microscopy, image analysis, sedimentation and such other methods known to one skilled in the art. Particle size distribution information can be obtained from the values $D_{10}$, $D_{50}$, and $D_{90}$, such as can be generated from a Malvern particle size determination Without wishing to be bound by any theory, the applicants believe that the delivery of drug through nanodispersion comprising nanoparticles having mean size less than 300 nm, leads to enhanced internalization and accumulation of the drug in the target tumor tissues and cells. Such increased internalization levels provides a potent treatment strategy for curing tumors associated with cancer.

According to one embodiment of the present invention, the particle size of the nanoparticles is in the range of 10 nm to 275 nm. In preferred embodiments of the present invention, the particle size is less than 200 nm. In most preferred embodiments of the present invention, the particle size is in the range of 10 nm to 200 nm.

The present invention provides a nanodispersion comprising nanoparticles having a mean size less than 300 nm dispersed in a vehicle comprising a water miscible solvent and water, said nanoparticles comprising one or more taxane derivative, a polymer and a surfactant comprising a mixture of fatty acids or its salts and sterol or its derivatives or its salts.

The present invention also provides a solution comprising one or more taxane derivative, a polymer and a surfactant comprising a mixture of fatty acids or its salts and sterol or its derivatives or its salts in a water miscible solvent, which upon dilution with an aqueous liquid vehicle gives nanodispersion.

The Nanoparticles of the present invention have a mean particle size less than 300 nms, wherein the said particles comprises one or more taxane derivative, surfactant comprising a mixture of sterol or its derivatives or its salts and fatty acid or it salts and a polymer.

The taxane derivative, as mentioned in the embodiments of the present invention are those compounds which essentially have a taxane skeleton and are complex diterpenoid natural product derived principally from natural sources such as bark of the Yew tree, *taxus brevifolia* or from cell culture, or chemically synthesized molecules. The principal mechanism of action of the taxane class of drugs is the inhibition of the microtubule function. It does this by stabilizing GDP-bound tubulin in the microtubule. Microtubules are essential to cell division, and taxanes therefore stop this—called a "frozen mitosis".

Most prominent representatives of this group which are used in the compositions of the present invention include paclitaxel and docetaxel and their pharmaceutically acceptable salts, derivatives, analogs and isomers such as 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, and the like and mixtures thereof.

Paclitaxel is a natural product with antitumor activity. Paclitaxel is obtained via a semisynthetic process from *taxus brevifolia* and/or *taxus baccata*. The chemical name for paclitaxel is 5α,20-Epoxy-1,2α,4,7β,10β,13α-hexahydroxytax-11-en-9-one 4,10-diacetate 2-benzoate 13-ester with (2R,3S)—N-benzoyl-3-phenylisoserine. Paclitaxel is available in the United States of America as TAXOL Injection. Paclitaxel is indicated as first-line and subsequent therapy for the treatment of advanced carcinoma of the ovary. As first-line therapy, paclitaxel is indicated in combination with cisplatin. Paclitaxel is also indicated for the adjuvant treatment of node-positive breast cancer administered sequentially to standard doxorubicin-containing combination chemotherapy. Paclitaxel is also indicated for the treatment of breast cancer after failure of combination chemotherapy for metastatic disease or relapse within 6 months of adjuvant chemotherapy. Paclitaxel, in combination with cisplatin, is also indicated for the first-line treatment of non-small cell lung cancer in patients who are not candidates for potentially curative surgery and/or radiation therapy. Paclitaxel is also indicated for the second-line treatment of AIDS-related Kaposi's sarcoma.

Docetaxel is another antineoplastic agent belonging to the taxoid family. It is prepared by a semisynthetic method beginning with a precursor extracted from the renewable needle biomass of yew plants. The chemical name for docetaxel is (2R,3S)—N-carboxy-3-phenylisoserine,N-tert-butylester, 13-ester with 5β-20-epoxy-1,2α,4,7β,10β,13α-hexahydroxytax-11-en-9-one 4-acetate 2-benzoate, trihydrate. Docetaxel is available in the United States of America as TAXOTERE® Injection concentrate. Docetaxel as a single agent is indicated for the treatment of patients with locally advanced or metastatic non-small cell lung cancer after failure of prior platinum-based chemotherapy. Docetaxel in combination with cisplatin is indicated for the treatment of patients with unresectable, locally advanced or metastatic non-small cell lung cancer who have not previously received chemotherapy for this condition. Docetaxel in combination with prednisone is indicated for the treatment of patients with androgen independent (hormone refractory) metastatic prostate cancer. Docetaxel in combination with cisplatin and fluorouracil is indicated for the treatment of patients with advanced gastric adenocarcinoma, including adenocarcinoma of the gastroesophageal junction, who have not received prior chemotherapy for advanced disease. Docetaxel in combination with cisplatin and fluorouracil is indicated for the induction treatment of patients with inoperable locally advanced squamous cell carcinoma of the head and neck. The embodiments of the present invention comprise paclitaxel in an amount ranging from about 0.001 mg/ml to about 15.0 mg/ml, more preferably from about 0.1 mg/ml to about 10.0 mg/ml and most preferably from about 1.5 mg/ml to about 5.0 mg/ml. Docetaxel is used in the embodiments of the present invention in an amount ranging from about 0.001 mg/ml to about 10.0 mg/ml, more preferably from about 0.1 mg/ml to about 1.0 mg/ml and most preferably from about 0.3 mg/ml to about 0.7 mg/ml.

The nanodispersion comprising nanoparticles may further comprise an additional therapeutically active agent selected from the group consisting of an anti-inflammatory agent, an anti-histaminic agent, a 5-HT$_3$ antagonist, a H$_2$-receptor antagonist, a vitamin and mixtures thereof. Anti-inflammatory agents that may be used in the compositions of the present invention may be selected from steroidal anti-inflammatory drugs and non-steroidal anti-inflammatory drugs. The embodiments of the present invention preferably comprise steroidal anti-inflammatory drugs such as glucocorticoids. Examples of glucocorticoids that may be used in the compositions of the present invention may be selected from cortisol or hydrocortisone, prednisone, prednisolone, dexamethasone, betamethasone, budesonide, triamcinolone and the like and mixtures thereof. In a preferred embodiment of the present invention, dexamethasone is used as the anti-inflammatory agent. Anti-histaminic agent or histamine antagonists that may be used in the compositions of the present invention may be selected from first generation anti-histaminic agents such as ethylenediamines (mepyramine, antazoline), ethanolamines (diphenhydramine, carbinoxamine, clemastine, dimenhydrinate), alkylamines (pheniramine, chlorpheneramine, dexchlorpheniramine, triprolidine), piperazines (cyclizine, chlorcyclizine, hydroxyzine, meclizine), tricyclics and tetracyclics (promethazine, alimemazine, cyproheptadine, azatadine, ketotifen) and the like; second generation anti-histaminic agents such as acrivastine, astemizole, cetirizine, loratidine, mizolastine, terfenadine, azelastine, levocabastine, olapatidine and the like; third generation anti-histaminic agents such as levocetrizine, desloratidine, fexofenadine and the like and mixtures thereof. 5-HT$_3$ antagonist that may be used in the compositions of the present invention may be selected from ondansetron, granisetron, dolasetron, tropisetron, palonosetron, alosetron, cilansetron and the like and mixtures thereof. H$_2$-receptor antagonist or H$_2$-antagonist that may be used in the compositions of the present invention may be selected from cimetidine, ranitidine, nizatidine, famotidine, roxatidine, burimamide, metiamide and the like and mixtures thereof. Vitamins that may be used in the compositions of the present invention may be selected from fat soluble vitamins such as vitamin A, vitamin D, vitamin E and vitamin K and water soluble vitamins such as vitamin C and vitamin B including vitamin (B1: thiamine; B2: riboflavin; B3: niacin; B5: pantothenic acid; B7: biotin; B9: folic acid; B12: cyanocobalamin) and mixtures thereof. In one embodiment of the present invention the vitamin used is Vitamin D.

The nanoparticles present in the nanodispersion of the present invention comprises one or more polymer. The polymer(s) that are suitable for the nanoparticles of the present invention are preferably, water soluble. The examples of the water soluble polymers includes, but are not limited to, polyvinylpyrrolidone, poloxomer, polyethylene glycol, polyvinyl alcohol, sodium alginate, sodium hyaluronate, gellna gum, carragenan, xanthan gum, dextran sulfate, chondroitin sulfate, pectinates, heparins, methacrylic acid copolymers, dermatan sulfate, cellulosic polymers such as sodium carboxymethyl cellulose, hydroxyethyl cellulose, hydroxypropyl methyl cellulose and the like and mixtures thereof.

Polyvinylpyrrolidone is a tertiary amide polymer having linearly arranged monomer units of 1-vinyl-2-pyrrolidone, hereinafter designated PVP, and also known as Povidone. It is commercially available as a series of products having mean molecular weights ranging from about 10,000 to about 700, 000. The various products are marketed according to average molecular weights designated K-values; e.g. GAF Corporation supplies PVP having the following K-values:

| K-value | Average Molecular Weight |
|---------|--------------------------|
| 15      | about 10,000             |
| 30      | about 40,000             |
| 60      | about 160,000            |
| 90      | about 360,000            |

Another supplier, BASF provides different water soluble grades of polyvinyl pyrrolidone as Kollidon with grades having for eg, molecular weight of 2000 to 3000 (Kollidon 12 PF), 7000-11,000 (Kollidon 17 PF), 28,000-34,000 (Kollidon 25), 1,000,000-1,5000,000 (Kollidon 90 F). In the embodiments polyvinylpyrrolidone is used as a water soluble polymer. The grades of polyvinylpyrrolidone suitable for the present invention include grades having a molecular weight in the range from about 1,000 to about 45,000, preferably, from about 4,000 to about 30,000. According to one embodiment of the present invention, the amount of polymer used in the nanodispersion ranging from about 0.001% w/v to about 20% w/v. The polymer is preferably used in an amount ranging from about 0.01% w/v to about 5.0% w/v. Most preferably, it is used in an amount ranging from about 0.01% w/v to about 1.0% w/v.

The nanodispersion of the present invention comprises one or more surfactants. The term surfactant is a blend of "surface active agent". Surfactants are molecules, which comprises a water-soluble (hydrophilic) and a lipisoluble (lipophilic) part. The surfactants that are used in the nanodispersion of the present invention comprises a mixture of fatty acid or its salts and sterol or its derivatives or its salts.

The term fatty acids includes aliphatic (saturated or unsaturated) monocarboxylic acids derived from or contained in esterified form, in an animal or vegetable fat, oil or wax. Examples of fatty acids or its salts that may be used in the compositions of the present invention include but are not limited to fatty acids or its salts having 'n' number of carbon atoms wherein 'n' ranges from about 4 to about 28. The fatty acid may be a saturated fatty acid or an unsaturated fatty acid, and their salt and combinations thereof. The saturated fatty acid and its salts may be selected from butyric acid, caproic acid, capylic acid, capric acid, lauric acid, myristic acid, palmitic acid, stearic acid, arachidic acid, behenic acid, sodium caprylate, sodium laurate, sodium myristate, sodium palmitate and the like and/or mixtures thereof. The unsaturated fatty acid and its salts may be selected from myristoleic acid, palmitoleic acid, oleic acid, linoleic acid, alpha linolenic acid, arachidonic acid, eicosapentaenoic acid, erucic acid, docosahexaenoic acid, sodium oleate, sodium arachidonate and the like and/or mixtures thereof.

Examples of sterol or its derivative or its salts that may be used in the nanodispersion or nanoparticles of the present invention may be acid esters of sterols. The sterols that may be suitable according to the present invention include, but are not limited to, cholesterol, phytosterols, ergosterol, bile acids salts and mixtures thereof. Acid salts of cholesterol that may be used include, but are not limited to, cholesteryl sulfate, cholesterol acetate, cholesterol chloroacetate, cholesterol benzoate, cholesterol myristate, cholesterol hemisuccinate, cholesterol phosphate, cholesterol phosphate, phosphonate, borate, nitrate, cholesterol cinnamate, cholesterol crotanoate, cholesterol butyrate, cholesterol heptanoate, cholesterol hexanoate, cholesterol octanoate, cholesterol nonanoate, cholesterol decanoate, cholesterol oleate, cholesterol propionate, cholesterol valerate, dicholesteryl carbonate and the like and mixtures thereof. Phytosterols that may be used in the compositions of the present invention include sitosterol, campesterol, stigmasterol, brassicasterol and its derivatives, salts and mixture thereof. For example, Phytosterols* marketed by Sigma, U.S.A. containing bsitosterol, campesterol and dihydrobrassicasterol. Bile acids include cholic acid, chenodeoxycholic acid, deoxycholic acid, glycocholic acid, taurocholic acid, ursodeoxycholic acid and its derivatives, salts and mixture thereof. The sterols can also be esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate.

According to one embodiment of the present invention, the nanoparticles comprise a surfactant which is a mixture of sterol or its derivatives or its salts and fatty acids or its salts. In another preferred embodiment, the nanoparticles comprise of cholesterol ester of polar acids. In one preferred embodiments, the surfactant used in the nanodispersion is a mixture of caprylic acid and cholesteryl sulfate. Caprylic acid, also known as octanoic acid may be used in the embodiments in an amount ranging from about 0.001% w/v to about 5.0% w/v, more preferably from about 0.01% w/v to about 1.0% w/v and most preferably from about 0.01% w/v to about 0.5 w/v. Cholesteryl sulfate is used in the embodiments of the present invention in an amount ranging from about 0.001% w/v to about 5.0% w/v, more preferably from about 0.01% w/v to about 1.0% w/v and most preferably from about 0.01% w/v to about 0.5% w/v.

It has been found surprisingly that this particular mixture of surfactants provides a nanodispersion of taxane derivatives that remains stable for more than 6 hours even at low ratios of surfactant to taxane derivatives. In the nanodispersion of the present invention, the ratio of surfactant to taxane derivatives is about 1:5 to about 1:10. Nanodispersion of the present invention remains stable for at least 6 hours particularly, nanodispersion comprising paclitaxel was found to remain stable for 24 hours whereas the nanodispersion comprising docetaxel was found to remain stable for 8 hours.

According to another preferred embodiment, the surfactant used is selected from oleic acid and cholesteryl sulphate and/or mixtures thereof.

According to another embodiment of the present invention, the surfactant used is selected from saturated fatty acid and bile acid or bile salt and/or mixtures thereof. According to preferred embodiment, the surfactant used is selected from the group consisting of caprylic acid and sodium glycocholate or ursodeoxycholic acid and/or mixtures thereof.

Bile salts when used are employed in an amount ranging from about 0.001% w/v to about 5.0% w/v, more preferably from about 0.01% w/v to about 1.0% w/v and most preferably from about 0.01% w/v to about 0.75% w/v.

The compositions of the present invention may further comprise low amounts of lecithins/phospholipids and/or their derivatives. By the term low amounts' as used herein means that the ratio of phospholipids to taxane derivative is about 1:4 to about 1:10, that even if phospholipids are used they are used in very low amount i.e compared to the amount of taxane derivative the amount of phospholipids is very low. Generally, the prior art compositions that are liposomal, require large amounts of phospholipids compared to the amount of the drug.

In some embodiments when phospholipids are used in small amounts, the examples of such phospholipids, include, but are not limited to, lecithins natural, partially hydrogenated or hydrogenated lecithin or sphingolipids. Natural lecithins inturn are mixtures of different phospholipids. The phospholipids that may be used in the compositions of the present invention is selected from phosphatidyl choline, (dimyristoylphosphatidyl choline, dipalmitotylphosphatidyl choline, distearyloylphosphatidyl choline, dioleoylphosphatidyl choline, dilauryloylphosphatidyl choline, 1-palmitoyl-phosphatidyl choline, 1-myristoyl-2-palmitoyl phosphatidyl choline, 1-palmitoyl-2-myristoyl phosphatidyl choline, 1-stearoyl-2-palmitoyl phosphatidyl choline); phosphatidyl ethanolamine (dimyristoyl phosphatidyl ethanolamine, dipalmitoyl phosphatidyl ethanolamine, distearoyl phosphatidyl ethanolamine, lysophatidylethanolamine); sphingomyelins (brain sphingomyelin, dipalmitoyl sphingomyelin); lysolecithin; cerebrosides and the like and mixtures thereof. Further polyethylene glycol derivatives of lipids such as polyethylene glycol-distearoyl phosphatidylethanolamine (PEG-DSPE), methoxypolyethylene glycol-distearoyl phosphatidylcholine m-PEG-DSPC and the like and mixtures thereof may also be used in the compositions of the present invention. Preferably, the butylenesids that may be used in the compositions of the present invention is m-PEG-DSPE (methoxy polyethylene glycol-disteroyl phosphatidyl ethanolamine).

In one embodiment of the present invention, the phospholipid used is—mPEG-DSPE. It is used in an amount ranging from about 0.001% w/v to about 10.0% w/v, more preferably from about 0.01% w/v to about 5.0% w/v and most preferably from about 0.03% w/v to about 0.5% w/v.

The non-aqueous solvent used in the compositions of the present invention is one in which the taxane derivative is relatively soluble. The non aqueous solvent is miscible with water or aqueous solvents. Examples of such water miscible solvents used in the present invention includes, but are not limited to, alcohols such as ethanol, n-propanol, isopropanol; glycols such as ethylene glycol, propylene glycol, butylene glycol and its derivatives; polyethylene glycols like PEG 400 or PEG 3350; polypropylene glycol and its derivatives such as PPG-10 butanediol, PPG-10 methyl glucose ether, PPG-20 methyl glucose ether, PPG-15 stearyl ether; glycerol; glycofurol and the like and mixtures thereof.

In one embodiment of the present invention, the non-aqueous solvent may be selected from the group consisting of alcohols, polyethylene glycols and/or mixtures thereof. In preferred embodiment of the present invention, a mixture of ethanol and PEG (polyethylene glycol) is used as the water miscible solvent. Ethanol is used in the nanodispersion composition of the present invention in an amount ranging from about 0.001% w/v to about 5% w/v, more preferably from about 0.05% w/v to about 0.5% w/v and most preferably from about 0.1% w/v to about 0.25% w/v. Polyethylene glycols which are used preferably, include PEG-400 and PEG-3350. PEG-400 is used in the embodiments of the present invention in an amount ranging from about 0.01% w/v to about 20.0% w/v, more preferably from about 0.05% w/v to about 5.0% w/v and most preferably from about 1.0% w/v to about 2.5% w/v. PEG-3350 is used in the embodiments of the present invention in an amount ranging from about 0.001% w/v to about 10.0% w/v, more preferably from about 0.05% w/v to about 5.0% w/v and most preferably from about 0.1% w/v to about 3% w/v.

Generally, it is desirable that a taxane pre-concentrate i.e the solution upon dilution with the aqueous vehicle gives a nanodispersion that remains stable for at least about 4 hours. This time is the time during which the nano-dipersion may be administered to the patient in the form of infusion. Thus, it is always desirable to achieve minimum of 4 hours stability of the nanodispersion of the present invention. The vehicle may further comprise about 5% to about 10.0% w/v dextrose solution in water for injection or any other pharmaceutically acceptable intravenous aqueous liquid vehicle and mixtures thereof. One of the embodiments of the present invention wherein taxane derivative is paclitaxel, the aqueous vehicle further comprises 5% dextrose solution in order to improve this stability but additional stabilizers may also be present in the aqueous phase. Examples of such stabilizers are hetastarch, dextran, sodium hyaluronate, glutathione, ornithin-L-aspartate and the like and mixtures thereof. In another embodiment, it was found that use of 0.01% of arginine in 5% dextrose solution gave a nanodispersion of docetaxel that was stable for 8 hours, whereas use of 1% histidine in 5% dextrose solution resulted in a nanodispersion of docetaxel that was stable for 5 hours. In embodiments wherein docetaxel is used as the taxane derivative, the aqueous vehicle may further comprise hetastarch, dextran, sodium hyaluronate, glutathione, ornithine-aspartate, amino acids such as histidine, arginine and the like and mixtures thereof. These additional stabilizers may be present in amounts ranging from about 0.02% to about 5% of the aqueous vehicle. In one preferred embodiment, it was found that the use of 0.5% of hetastarch in 5% dextrose solution for a nanodispersion of docetaxel was stable in terms of particle size for more than 5 hours.

The nanodispersion of taxane derivatives of the present invention may be typically prepared by any one of the processes listed below:

1) The therapeutically active ingredient (taxane derivative and/or other agents), polymer(s) and surfactant(s) selected from fatty acids or its salts, sterol or its derivatives or its salts and mixtures thereof is dissolved in water misbicle solvent such as ethanol and/or PEG, along with stirring and heating to obtain a concentrated solution of the drug. The solution so obtained is filtered through a membrane filter. To this solution, an aqueous liquid vehicle (5% dextrose solution) is added slowly and the mixture is shaken/agitated, thus leading to the formation of the nanodispersion of the present invention. The nanodispersion so formed is optionally homogenized and/or sonicated, filtered or lyophilized. The lyophilized powder of the medicament can be reconstituted with the aqueous medium, reforming nanodispersion of the present invention, prior to administration to the patients.

2) The taxane derivative, polymer(s) and surfactant(s) selected from fatty acids or its salts, sterol or its derivatives or its salts and mixtures thereof is dissolved in water miscible solvent such as ethanol and/or PEG along with stirring and heating to obtain a concentrated solution of the drug. The solution so obtained is filtered through a membrane filter and is added to an aqueous medium (5% dextrose solution) and the mixture is shaken/agitated, thus leading to the formation of the nanodispersion of the present invention. The nanodispersion so formed is optionally homogenized and/or sonicated, filtered or lyophilized The lyophilized powder of the medicament can be reconstituted with the aqueous medium, reforming nanodispersion of the present invention, prior to administration to the patients.

3) The taxane derivative and surfactant(s) comprising a mixture of fatty acids or its salts and sterol or its derivatives or its salts is dissolved in water miscible solvent such as ethanol and/or PEG by slightly warming at 40° C. in a round bottomed flask, and the solvent is evaporated to form a thin film of the drug. The polymer(s) is dissolved in required quantity of an aqueous medium and this solution is added to the film with gentle agitation and shaking for 3-4 hours, thus leading to the formation of the nanodispersion of the present invention. The nanodispersion so formed is optionally homogenized and/or sonicated, filtered and lyophilized The lyophilized powder of the medicament can be reconstituted with the aqueous medium, reforming nanodispersion of the present invention, prior to administration to the patients.

As the nanodispersion of the present invention is a colloidal nanodispersion of taxane derivative comprising nanoparticles having a mean size less than 300 nm, they were analyzed for physical and chemical stability. It was observed that the particles do not aggregate upon storage at room temperature for about 8 hours to about 24 hours and the nanodispersion shows no sign of change in appearance, inferring that the nanodispersion is stable for the desired period of time before and during administration.

Also, when a solution of a taxane derivative and/or other agents in water miscible solvent was tested, it was observed that the solution remains physically and chemically stable for at least a period of 3 months, with no significant change in assay of the drug and no substantial aggregation or change in appearance of the formulation. The observations are illustrated in the upcoming examples.

The nanodispersion of the present invention can be provided as a kit having two or more containers, for example two containers, wherein the first container comprising a solution of a taxane derivative, a polymer and a surfactant comprising a mixture of fatty acids or its salts and sterol or its derivatives or its salts in a water miscible solvent, and a second container comprising an aqueous liquid vehicle, such that on addition of contents of second container to the contents of the first container or vice versa, with mild agitation or shaking, results in the formation of nanodispersion of the present invention and is suitable for intravenous administration. An additional container may contain a third component for mixing prior to formation of taxane nanodispersion or after nanodispersion of the said taxane is formed.

The present invention also provides a kit having two containers, the first container comprising a lyophilized form of the nanodispersion and a second container comprising an aqueous liquid vehicle such that prior to administration to the patients, the contents of second container can be added to the contents of the first container or vice versa with mild agitation or shaking, resulting in the formation of nanodispersion of the present invention.

Administering the nanodispersion of the present invention to patients in need thereof, will provide an efficient method of treatment of various types of cancers known in the art.

The efficacy and toxicity of the nanodispersion of the present invention were compared to the commercially available taxel products such as Abraxane®, Oncotaxel® and the like. The efficacy was assessed based on the following parameters:

1. Tumor evaluation: Tumors were evaluated for reduction in tumor volume (mm3) with respect to time in days. The tumors were evaluated for a time period of 42 days.
2. Percentage T/C=(mean tumor volume of drug treated group on day X/mean tumor volume of drug treated group on day X)×100
3. Tumor Regression: Tumor regression in an experimental animal tumor models important end points in clinical relevance. The tumor regression was recorded as partial (PR) if the tumor volume decreased to less than 50% of the tumor volume at the start of the treatment without dropping below a measurable size, or as complete (CR) if the tumor burden has become impalpable.
4. Specific tumor growth delay (SGD) is defined as the ratio of the difference in time for drug treated and control tumors to reach a given volume (v) and the time for control tumors to reach the same volume (v) wherein the V being a tumor volume after two volume doublings from initial tumor volume at the start of the treatment and Tv being the time for the drug treated or control groups to reach the given volume. If V value value was not achieved in the test or reference group animal until day 45, same value *day 45) was considered at Tv for that animal. The test is considered to be efficacious if the SGD parameter is more than 1.
5. The body weight changes were calculated as (weight of the animal on day X— weight of the animal on day 0 to the weight of the animal on day 0)×100.
6. Survival analysis was done by Kaplan Meier method. P values<0.05 was considered significant.

Although, the efficacy of the nanodispersion of the present invention was assessed by the above mentioned parameters, any other suitable or similar method of testing may be adapted to determine the efficacy of the nanodispersion. It was found that the tested nanodispersion of the present invention were efficacious as exemplified in examples 27, 28 and 29.

The toxicity of the nanodispersion of the present invention was determined by administering the test to CD-1 Mice by Intravenous Route. After last injection, animals were observed for 1 h and between 4-6 h of post-dosing. Thereafter, mice were observed twice daily for clinical symptoms and mortality for 15 days. Body weights of all surviving animals were recorded on days 1, 7 and 14 post-dosing. On day 15, necropsy of surviving animals was performed and the gross pathology, if any, was recorded. The results of the toxicity studies have been described in details in example 25 and 26 for paclitaxel nanodispersion and docetaxel nanodispersion, respectively.

While the present invention is disclosed generally above, additional aspects are further discussed and illustrated with reference to the examples below. However, the examples are presented merely to illustrate the invention and should not be considered as limitations thereto.

EXAMPLE 1-5

Nanodispersions of the present invention are described in Table 1 below.

TABLE 1

| S. No. | Ingredients | Quantity (% w/v) | | | | |
|---|---|---|---|---|---|---|
| | | Example 1 | Example 2 | Example 3 | Example 4 | Example 5 |
| 1 | Paclitaxel | 0.15 | 0.15 | 0.15 | 0.15 | 0.15 |
| 2 | Cholesteryl sulfate | 0.01 | 0.01 | 0.01 | 0.02 | 0.04 |
| 3 | Caprylic acid | 0.0125 | 0.0125 | 0.0125 | 0.025 | 0.05 |
| 4 | Polyvinylpyrrolidone (PVP) K-30 | 0.125 | 0.0625 | 0.0325 | 0.125 | 0.125 |
| 5 | Ethanol | 0.14825 | 0.14825 | 0.14825 | 0.14825 | 0.14825 |
| 6 | PEG-400 | 2.0 | 2.0 | 2.0 | 2.0 | 2.0 |
| 7 | Dextrose (5%) | qs. 100.0 | qs. 100.0 | qs. 100.0 | qs. 100.0 | qs. 100.0 |

Procedure:
  Drug, cholesteryl sulfate, caprylic acid and PVP K-30 were weighed accurately in a vial.
  Contents were dissolved in the required quantity of absolute ethanol and PEG-400 with stirring and by heating at 45° C. to obtain a solution.
  The solution was filtered through 0.2µ PVDF membrane filter.
  Dextrose solution (5%) was then added slowly to the vial containing the solution of drug and shaken gently to get a transparent to translucent nanodispersion.
  pH of the nanodispersion is checked by using pH Meter (Mettler Toledo-seven easy).
  Particle size of the nanodispersion is measured by Particle size analyzer (Nano-ZS, Malvern)
  The visual appearance, pH and the particle size of the compositions as observed are summarized in table 2 below.

TABLE 2

| | Observation | | | | |
|---|---|---|---|---|---|
| | Example 1 | Example 2 | Example 3 | Example 4 | Example 5 |
| | Appearance | | | | |
| Initial | Almost transparent to transluscent dispersion | Almost transparent to transluscent dispersion | Almost transparent to transluscent dispersion | Almost transparent to transluscent dispersion | Almost transparent to transluscent dispersion |
| 24 hours at RT | Almost transparent to transluscent dispersion | Almost transparent to transluscent dispersion | Almost transparent to transluscent dispersion | Almost transparent to transluscent dispersion | Almost transparent to transluscent dispersion |
| pH | 3.86 | 4.0 | 4.0 | 4.0 | 4.0 |
| | Particle Size (nm) | | | | |
| Initial | 127 | 146 | 179 | 136 | 122 |
| 3 hour | 134 | 148 | 156 | 138 | 158 |
| 24 hour | 128 | 154 | 158.2 | 169 | 169 |

It can be seen that the nanodispersions of the present invention are physically stable, with no substantial aggregation or change in appearance of the formulation on storage for 24 hours at room temperature.

The nanodispersion composition of these examples contains 150 mg/100 ml of paclitaxel. For the human dose of approximately 300 mg of paclitaxel for a 70 kg person, 200 ml of the each nanodispersion composition can be administered to the patient. Thus 20 to 80 mg of the cholesteryl sulfate, 25 to 100 mg caprylic acid, 65 to 250 mg of PVP and about 300 mg ethanol would be given with a single adult dose of paclitaxel composition of Examples 1 to 5. Thus the composition of the present invention provides nanosized particles with very low amounts of excipients co-administered with the active agent.

Pharmaceutical compositions as described in examples 6-7 below are concentrated solutions which have to be diluted several times with a diluent (5% w/v dextrose solution) to obtain a nanodispersion of the present invention before administration to the patient.

Although the invention has been described in terms of particular embodiments and applications, one of ordinary skill in the art, in light of this teaching, can generate additional embodiments and modifications without departing from the spirit of or exceeding the scope of the claimed invention. It should be emphasized that the above-described embodiments of the present invention, particularly any "preferred" embodiments, are merely possible examples of the invention of implementations, merely set forth for a clear understanding of the principles of the invention.

Accordingly, it is to be understood that the drawings and descriptions herein are preferred by way of example to facilitate comprehension of the invention and should not be construed to limit the scope thereof.

EXAMPLE 6-7

Pharmaceutical compositions of the present invention as concentrated solution of taxane derivative are described in Table 3 below.

TABLE 3

| Sr. No. | Ingredients | Quantity (% w/w) | |
|---|---|---|---|
| | | EXAMPLE 6 (Drug conc: 60 mg/gm) | EXAMPLE 7 (Drug conc: 100 mg/gm) |
| 1 | Paclitaxel | 6.0 | 10.0 |
| 2 | Cholesteryl sulfate | 0.400 | 0.66 |
| 3 | Caprylic acid | 0.500 | 0.830 |

TABLE 3-continued

| Sr. No. | Ingredients | Quantity (% w/w) | |
|---|---|---|---|
| | | EXAMPLE 6 (Drug conc: 60 mg/gm) | EXAMPLE 7 (Drug conc: 100 mg/gm) |
| 4 | Polyvinylpyrrolidone (PVP) K-30 | 5.0 | 4.16 |
| 5 | Ethanol | 6.0 | 10.0 |
| 6 | PEG-400 | Qs to 100.0 | Qs to 100.0 |

Procedure:
- Drug, cholesteryl sulfate, caprylic acid and PVP K-30 were weighed accurately in a glass vessel.
- Contents were dissolved in the required quantity of absolute ethanol and PEG-400 with stirring and by heating at 45° C. to obtain a concentrated drug solution.
- The solution was filtered through 0.2 u PVDF membrane filter.
- The solution of example-6 was filled in vials (1 gm per vials containing 60 mg drug) and charged for stability.

Stability samples were analyzed in the form of nanodispersion. Dextrose solution (5% w/v) (40 ml) was slowly added to the vial containing the drug concentrate (60 mg drug) with gentle shaking to get a transparent to transluscent nanodispersion of drug having dilution of 1.5 mg/ml. Nanodispersion was analyzed for the following tests: Appearance, Assay of Drug, pH (Mettler Toledo-seven easy, pH Meter) and Particle size (Nano-ZS, Malvern Particle size analyzer), described in table 4 below.

TABLE 4

Stability Data of Example-6

| Stability condition | Concentrated drug solution Appearance | Nanodispersion Appearance | Assay of drug | pH | Particle size (nm) Initial | Particle size (nm) After 24 h |
|---|---|---|---|---|---|---|
| Initial | Clear, colorless, viscous liquid | Almost transparent to transluscent nanodispersion | 96.59 | 3.97 | 152 | 146 |
| 25° C./60% RH | | | | | | |
| 1 M | Clear, colorless, viscous liquid | Almost transparent to transluscent nanodispersion | 93.55 | 4.00 | 133 | 149 |
| 3 M | Clear, colorless, viscous liquid | Almost transparent to transluscent nanodispersion | 94.07 | 4.00 | 165 | 162 |
| Fridge 2-8° C. | | | | | | |
| 1 M | Clear, colorless, viscous liquid | Almost transparent to transluscent nanodispersion | 94.86 | 3.96 | 132 | 127 |
| 3 M | Clear, colorless, viscous liquid | Almost transparent to transluscent nanodispersion | 94.47 | 3.99 | 159 | 165 |

There was no change in assay of paclitaxel over three months inferring that the formulation is chemically stable. Also, it can be seen that the compositions of the present invention are physically stable, with no substantial aggregation or change in appearance of the formulation on storage.

EXAMPLE 8

Pharmaceutical compositions of the invention using PVP K-12 are described in Table 5 below. The procedure for the preparation of nanodispersion is same as in example 1-7.

TABLE 5

| S. No. | Ingredients | Quantity (% w/v) |
|---|---|---|
| 1 | Paclitaxel | 0.15 |
| 2 | Cholesteryl sulfate | 0.01 |
| 3 | Caprylic acid | 0.0125 |
| 4 | Polyvinylpyrrolidone (PVP) K-12 | 0.125 |
| 5 | Ethanol | 0.14825 |
| 6 | PEG-400 | 2.0 |
| 7 | Dextrose (5%) | qs. 100.0 |

The visual appearance, pH and the particle size of the compositions were observed and are summarized in table 6 below.

TABLE 6

| Observations | |
|---|---|
| Appearance | |
| Initial | Almost transparent to translucent dispersion |
| 24 hours at RT | Almost transparent to translucent dispersion |
| pH | 4.0 |
| Particle Size (nm) | |
| Initial | 164 |
| 1 h | 169 |
| 3 h | 179 |
| 5 h | 177 |
| 24 h | 177 |

RT: room temperature

Stability samples were analyzed as described below and stability data is provided in Table 8.

Assay of drug was done in the concentrated drug solution. While for other observations, dextrose solution (5% w/v) (40 ml) was slowly added to the vial containing the drug concentrate (60 mg drug) with gentle shaking to get a transparent to transluscent nanodispersion of drug having dilution of 1.5 mg/ml. The nanodispersion was then analyzed for the following tests: Appearance, pH (Mettler Toledo-seven easy, pH Meter) and Particle size (Nano-ZS, Malvern Particle size analyzer)

TABLE 8

Stability Data of Example 9

| Stability condition | Pre concentrate Appearance | Assay | Nanodispersion Appearance | pH | Particle size (nm) Initial | After 8 h | After 24 h |
|---|---|---|---|---|---|---|---|
| Initial | Clear, colorless, viscous liquid | 97.02 | Almost transparent to transluscent nanodispersion | 3.87 | 149 | 156 | 160 |
| 25° C./60% RH | | | | | | | |
| 1 M | Clear, colorless, viscous liquid | 97.81 | Almost transparent to transluscent nanodispersion | 3.90 | 159 | 225 | 246 |
| 3 M | Clear, colorless, viscous liquid | 99.08 | Almost transparent to transluscent nanodispersion | 3.74 | 146 | 153 | 160 |
| 12 M | Clear, colorless, viscous liquid | 100.32 | Almost transparent to transluscent nanodispersion | 3.8 | 110 | 115 | 114 |
| Fridge 2-8° C. | | | | | | | |
| 1 M | Clear, colorless, viscous liquid | 98.02 | Almost transparent to transluscent nanodispersion | 3.92 | 140 | 150 | 150 |
| 3 M | Clear, colorless, viscous liquid | 98.02 | Almost transparent to transluscent nanodispersion | 3.72 | 97.9 | 109 | 111 |
| 12 M | Clear, colorless, viscous liquid | 99.10 | Almost transparent to transluscent nanodispersion | 3.75 | 113 | 119 | 113 |

RH: Relative Humidity.

It can be seen that the compositions of the present invention are physically stable, with no substantial aggregation or change in appearance of the formulation on storage for 24 hours at room temperature.

EXAMPLE 9

The compositions of the present invention as concentrated solution of taxane derivative is described in table 7 below.

TABLE 7

| Sr. No. | Ingredients | Quantity (% w/w) (Drug conc: 100 mg/gm) |
|---|---|---|
| 1 | Paclitaxel | 10.0 |
| 2 | Cholesteryl sulfate | 0.66 |
| 3 | Caprylic acid | 0.83 |
| 4 | Polyvinylpyrrolidone (PVP) K-12 | 8.33 |
| 5 | Ethanol | 10.0 |
| 6 | PEG-400 | Qs to 100.0 |

There was no change in assay of paclitaxel over 3 months inferring that the formulation is chemically stable on storage. Also, it can be seen that the compositions of the present invention are physically stable, with no substantial aggregation or change in appearance of the formulation on storage at various storage conditions. FIG. 4 (*a*) indicates a histogram showing particle size distribution of the nanodispersion at initial time and FIG. 4 (*b*) indicates the histogram showing the particle size distribution of the nanodispersion of paclitaxel example 9 when stored at room temperature for 24 hours. The histograms indicates that after a storage at room temperature for about 24 hours, the mean particle size was almost constant showing the stable nature of the nanodispersion.

EXAMPLE 10

A pharmaceutical composition of the present invention containing PEG-3350 is described in Table 9.

TABLE 9

| Sr. No. | Ingredients | Quantity (% w/v) |
|---|---|---|
| 1 | Paclitaxel | 0.15 |
| 2 | Cholesteryl sulfate | 0.01 |
| 3 | Caprylic acid | 0.0125 |
| 4 | Polyvinylpyrrolidone (PVP) K-30 | 0.0625 |
| 5 | Ethanol (% v/v) | 2.5 |
| 6 | PEG-3350 | 0.5 |
| 7 | Dextrose (5%) | Qs 100.0 |

Preparation:
  Drug, cholesteryl sulfate, caprylic acid, PVP K-30 and PEG 3350 were weighed in a vial.
  The contents of vial were dissolved in required quantity of absolute ethanol by stirring and heating at 45° C. until a clear solution is obtained.
  The above ethanolic solution was added slowly to dextrose solution (5%) with stirring to form a nanodispersion.
  pH of the nanodispersion is checked by using pH Meter (Mettler Toledo-seven easy).
  Particle size of the nanodispersion is checked by Particle size analyzer (Nano-ZS, Malvern Particle Size Analyzer.)
  The nanodispersion is filtered through 0.4µ membrane filter.
  20 ml of the above nanodispersion was filled into vial and lyophilized (Virtis).
  The visual appearance and the particle size of the nanodispersion before lyophilization was observed immediately after the nanodispersion was prepared and at 24 and 48 hours after storage at room temperature (RT). These are summarized in Table 10 below:

TABLE 10

| Observation | Appearance | Particle size (nm) |
|---|---|---|
| Initial | Translucent nanodispersion | 128 |
| 24 hours at RT | Translucent nanodispersion | 132 |
| 48 hours at RT | Translucent nanodispersion | 137 |

RT: room temperature

It can be seen that the composition of the present invention is physically stable with no substantial aggregation or change in appearance of the formulation on storage for 24 to 48 hours at room temperature.

Reconstitution of lyophilized cake: After lyophilization, cake obtained in the vial is dispersed by injecting in water for injection (20 ml) by gentle shaking to obtain paclitaxel nanodispersion having concentration of 1.5 mg/ml.

The contents per vial and characteristics of reconstituted nanodispersion are given respectively in Table 11 and 12 below:

TABLE 11

| Sr. No. | Ingredients | Quantity (mg/vial) |
|---|---|---|
| 1. | Paclitaxel | 30.0 |
| 2. | Cholesteryl sulphate | 2.0 |
| 3. | Caprylic acid | 2.5 |
| 4. | Polyvinylpyrrolidone (PVP) K-30 | 12.5 |
| 5. | PEG-3350 | 100.0 |

Each vial contained 30 mg paclitaxel in the composition. For the human dose of approximately 300 mg of paclitaxel for a 70 kg person, 10 vials of the above composition can be taken and reconstituted in 60 to 600 ml of the diluent such as WFI to obtain 0.5 to 5.0 mg/ml of paclitaxel infusion. This diluted composition if administered to the patient will contain 20 mg of cholesteryl sulphate, 25 mg of caprylic acid and 125 mg of PVP.

TABLE 12

| Observation after reconstitution. | Appearance | Particle size (nm) |
|---|---|---|
| Initial | Translucent nanodispersion | 217 |
| 24 hours at RT | Translucent nanodispersion | 225 |

It can be seen that the composition of the present invention is physically stable with no substantial aggregation and no change in appearance of the formulation, on storage for 24 hours at room temperature.

Example 11 and Comparative Examples I-III

TABLE 13

| | | Quantity (% w/v) | | | |
|---|---|---|---|---|---|
| Sr. | | EXAMPLE | COMPARATIVE | | |
| No. | Ingredients | 11 | I | II | III |
| 1 | Paclitaxel | | 0.15 | | |
| 2 | Cholesteryl sulphate | 0.01 | — | 0.01 | 0.01 |
| 3 | Caprylic acid | 0.0125 | 0.0125 | — | 0.0125 |
| 4 | Polyvinyl pyrroliodone (K-30) | 0.0625 | 0.0625 | 0.0625 | — |
| 5 | Ethanol | 0.1875 | 0.1875 | 0.1875 | 0.1875 |
| 6 | PEG-400 | 2.0 | 2.0 | 2.0 | 2.0 |
| 7 | Dextrose (5% w/v) | | 100 ml | | |

TABLE 14

OBSERVATIONS

| Appearance initial | Transparent, bluish tint | Uniform dispersion with bluish tint | Translucent with bluish tint | uniform dispersion with bluish tint |
|---|---|---|---|---|
| | Particle Size (nm) | | | |
| Initial | | 234 | 175 | 237 |
| 1 hours | | 243 | 176 | — |
| 3 hours | | 253 | 178 | 258 |
| 5 hours | | | Aggregates observed | |

EXAMPLE 12

Pharmaceutical compositions of the invention are further described in Table 15 and the observation for various parameters is described in table 16.

TABLE 15

| Sr. No. | Ingredients | EXAMPLE 12 Concentrated drug solution Quantity (% w/w) | EXAMPLE 12a Nano dispersion Quantity (% w/v) |
|---|---|---|---|
| 1 | Paclitaxel | 10.0 | 0.15 |
| 2 | Cholesteryl sulfate | 0.66 | 0.01 |
| 3 | Caprylic acid | 0.830 | 0.0125 |
| 4 | Polyvinylpyrrolidone (PVP) K-30 | 4.16 | 0.0625 |
| 5 | mPEG-Distearoyl phosphatidyl ethanolamine (mPEG-DSPE) | 4.16 | 0.0625 |
| 6 | Ethanol | 10.0 | 0.14825 |
| 7 | PEG-400 | Qs to 100 | 2.0 |
| 8 | Dextrose (5% w/v) | — | q.s. To 100.0 ml |

TABLE 16

| Observations | Example 12 | Example 12 a |
|---|---|---|
| pH | — | 4.0 |
| Zeta Potential | — | −32.4 |
| Appearance | | |
| Initial | Clear colourless viscous liquid | Almost transparent to transluscent nanodispersion |
| 24 hours at RT | Clear colourless viscous liquid | Almost transparent to transluscent nanodispersion |
| Particle Size (nm) | Clear solution | |
| Initial | | 146 |
| 1 h | | 146 |
| 3 h | | 146 |
| 5 h | | 147 |
| 8 h | | 147 |
| 24 h | | 130 |

EXAMPLE 13-14

Nanodispersion compositions of the present invention prepared by using oleic acid and stearic acid are described in Table 17 below:

TABLE 17

| | | Quantity (% w/v) | |
|---|---|---|---|
| Sr. No | Ingredients | EXAMPLE 13 (Drug conc: 1.5 mg/ml) | EXAMPLE 14 (Drug conc: 1.5 mg/ml) |
| 1 | Paclitaxel | 0.15 | 0.15 |
| 2 | Cholesteryl sulfate | 0.01 | 0.01 |
| 3 | Oleic acid | 0.0125 | — |
| 4 | Stearic acid | — | 0.0125 |
| 5 | Polyvinylpyrrolidone (PVP) K-30 | 0.0625 | 0.0625 |
| 6 | Ethanol | 0.14825 | 0.14825 |
| 7 | PEG-400 | 2.0 | 2.0 |
| 8 | Dextrose (5% w/v) | q.s. To 100 ml | q.s. To 100.0 ml |

The procedure for the preparation of these compositions is same as in example 1-5. The nanodispersions so obtained were almost transparent to translucent and had a mean particle size of 134 nm and 155 nm respectively.

EXAMPLE 15

Pharmaceutical composition of the present invention, prepared by using cholesterol is described in table 18 below.

TABLE 18

| Sr. No. | Ingredients | Quantity (% w/v) |
|---|---|---|
| 1. | Paclitaxel | 0.15 |
| 2. | Cholesterol | 0.01 |
| 3. | Caprylic acid | 0.830 |
| 4. | Polyvinylpyrrolidone (PVP) K-30 | 0.0625 |
| 5. | Ethanol | 0.14825 |
| 6. | PEG-400 | 2.0 |
| 7. | Dextrose (5% w/v) | q.s. To 100.0 ml |

Procedure:

Drug, cholesterol, caprylic acid and PVP K-30 were weighed accurately in a glass vessel.

Contents were dissolved in the required quantity of absolute ethanol and PEG-400 with stirring and by heating at 45° C. to obtain a concentrated solution.

The concentrated solution was filtered through 0.2μ PVDF membrane filter.

Dextrose solution (5% w/v) was slowly added to the vial containing the concentrated solution (100 mg drug) with gentle shaking to get a transparent to transluscent nanodispersion at the dilution of 1.5 mg/ml.

pH of the nanodispersion is checked by using pH Meter (Mettler Toledo-seven easy).

Particle size of the nanodispersion is checked by Particle size analyzer (Nano-ZS, Malvern).

The nanodispersion composition of this example was almost transparent to translucent and had a mean particle size of 217 nm.

EXAMPLE 16

Pharmaceutical compositions of the invention prepared by using bile acids/salts (Sodium glycocholate and Ursodeoxycholic acid) is described in table 19 below.

TABLE 19

| Sr. No. | Ingredients | Quantity (% w/v) (Drug concentration: 1.5 mg/ml) | |
| --- | --- | --- | --- |
| | | EXAMPLE 16 a | EXAMPLE 16 b |
| 1 | Paclitaxel | 0.15 | 0.15 |
| 2 | Sodium glycocholate | 0.75 | — |
| 3 | Ursodeoxycholic acid | — | 0.01 |
| 4 | Caprylic acid | 0.0125 | 0.0125 |
| 5 | Polyvinylpyrrolidone (PVP) K-30 | 0.0625 | 0.0625 |
| 6 | Ethanol | 0.14825 | 0.14825 |
| 7 | PEG-400 | 2.0 | 2.0 |
| 8 | Dextrose (5% w/v) | q.s. To 100.0 ml | q.s. To 100.0 ml |

Procedure:

Drug, bile acid/salt, caprylic acid, PVP K-30 were weighed accurately in a glass vessel.

Contents were dissolved in the required quantity of absolute ethanol and PEG-400 with stirring and by heating at 45° C. to obtain a concentrated solution.

The concentrated solution was filtered through 0.2µ PVDF membrane filter.

Dextrose solution (5% w/v) was slowly added to the vial containing the concentrated solution (100 mg drug) with gentle shaking to get a transluscent nanodispersion at the dilution of 1.5 mg/ml.

pH of the nanodispersion is checked by using pH Meter (Mettler Toledo-seven easy).

Particle size of the nanodispersion is checked by Particle size analyzer (Nano-ZS, Malvern).

The nanodispersion compositions so produced were almost translucent in appearance and had a mean particle size of 197 nm and 180 nm respectively.

EXAMPLE 17

Pharmaceutical compositions of the present invention containing PVP K-90 are described in Table 20.

TABLE 20

| Sr. No. | Ingredients | Quantity (% w/v) |
| --- | --- | --- |
| 1. | Paclitaxel | 0.15 |
| 2. | Cholesteryl sulfate | 0.01 |
| 3. | Caprylic acid | 0.0125 |
| 4. | Polyvinylpyrrolidone (PVP) K-90 | 0.0625 |
| 5. | Ethanol | 0.14825 |
| 6. | PEG-400 | 2.0 |
| 7. | Dextrose (5% w/v) | q.s. To 100.0 ml |

The procedure for the preparation is same as in example 1-5. The nano-dispersion composition so produced was almost transparent to translucent in appearance and had a mean particle size of 207 nm.

EXAMPLE 18

Pharmaceutical composition of the present invention containing hyaluronic acid salt is described in Table 21.

TABLE 21

| Sr. No. | Ingredients | Quantity (% w/v) |
| --- | --- | --- |
| 1 | Paclitaxel | 0.15 |
| 2 | Cholesteryl sulphate | 0.01 |
| 3 | Caprylic acid | 0.0125 |
| 4 | Sodium hyaluronate | 0.025 |
| 5 | Ethanol | 0.148 |
| 6 | PEG-400 | 2.0 |
| 7 | Dextrose (5% w/v) | q.s. To 100.0 ml |

Procedure:

Drug, cholesteryl sulphate and caprylic acid were weighed accurately in a glass vessel.

Contents were dissolved in the required quantity of absolute ethanol and PEG-400 with stirring and by heating at 45° C. to obtain a concentrated drug solution.

The solution was filtered through 0.2µ PVDF membrane filter.

Sodium hyaluronate was dissolved in Dextrose solution (5% w/v) and was slowly added to the vial containing the concentrated drug solution (30 mg), followed by the addition of remaining 5% w/v dextrose solution with gentle shaking to get a transluscent nanodispersion at the dilution of 1.5 mg/ml.

pH of the nanodispersion was checked by using pH Meter (Mettler Toledo-seven easy).

Particle size of the nanodispersion was checked by Particle size analyzer (Nano-ZS, Malvern. The nanodispersion composition so produced was almost translucent in appearance and had a mean particle size of 263 nm.

EXAMPLE 19

Pharmaceutical composition of the present invention containing polyglutamic acid salt is described in Table 22

TABLE 22

| Sr. No. | Ingredients | Quantity (% w/v) |
| --- | --- | --- |
| 1 | Paclitaxel | 0.15 |
| 2 | Cholesteryl sulphate | 0.01 |
| 3 | Caprylic acid | 0.0125 |
| 4 | Polyglutamic acid, sodium salt | 0.0625 |
| 5 | Ethanol | 0.148 |
| 6 | PEG-400 | 2.0 |
| 7 | Dextrose (5% w/v) | q.s. To 100.0 ml |

The procedure for the preparation of nanodispersion is same as in example 18. The nanodispersion composition so produced was almost translucent in appearance and had a mean particle size of 295 nm.

EXAMPLE 20

Pharmaceutical composition of the present invention containing an additional therapeutic agent dexamethasone is described in Table 23 below.

TABLE 23

| Sr. No. | Ingredients | Quantity (% w/v) |
| --- | --- | --- |
| 1 | Paclitaxel | 0.15 |
| 2 | Dexamethasone | 0.01 |
| 3 | Caprylic acid | 0.0125 |
| 4 | Polyvinylpyrrolidone (PVP) K-30 | 0.0625 |
| 5 | Ethanol | 0.148 |
| 6 | PEG-400 | 2.0 |
| 7 | Dextrose (5% w/v) | q.s. To 100 ml |

The nanodispersion composition so produced was almost translucent in appearance and had a mean particle size of 185 nm.

EXAMPLE 21

Pharmaceutical compositions of the present invention containing docetaxel are described in Table 24

TABLE 24

| Sr. No. | Ingredients | Quantity (% w/v) |
|---|---|---|
| 1 | Docetaxel | 0.15 |
| 2 | Cholesteryl sulfate | 0.01 |
| 3 | Caprylic acid | 0.0125 |
| 4 | Polyvinylpyrrolidone (PVP) K-30 | 0.125 |
| 5 | Ethanol | 0.14825 |
| 6 | PEG-400 | 2.0 |
| 7 | Dextrose (5%) | qs. 100.0 |

The nanodispersion of this example was prepared by the procedure given in examples 1-5. The nanodispersion was white in color with a bluish tinge and had a mean particle size of 172 nm.

The composition contains 1.50 mg/ml of the docetaxel. For the human dose of approximately 180 mg of docetaxel for a 70 kg person, 120 ml of the nanodispersion composition can be used for administration to the patient, so that the composition contained 180 mg of docetaxel. The patient to whom the composition of this example is administered, receives 12 mg of cholesteryl sulfate, 15 mg of caprylic acid, 150 mg of PVP and about 180 mg of ethanol. Thus the composition of the present invention provides nanosized particles with minimum amount of excipients co-administered with the active agent. Ethanol, if any, is in non addictive amounts.

EXAMPLE 22

Pharmaceutical composition of the present invention containing docetaxel is given below.

TABLE 25

| Sr. No. | Ingredients | | Quantity (% w/w) | | |
|---|---|---|---|---|---|
| | | | 21 (a) | 22 (b) | 23 (c) |
| 1 | Docetaxel | | 6.0 | 6.0 | 6.0 |
| 2 | Sodium cholesteryl sulfate | | 0.4 | 0.4 | 0.4 |
| 3 | Caprylic acid | | 0.40 | 0.40 | 0.40 |
| 4 | Polyvinylpyrrolidone (PVP) | K-12 | 5.0 | — | — |
| | | K-17 | — | 5.0 | — |
| | | K-30 | — | — | 5.0 |
| 5 | Ethanol | | 6.0 | 6.0 | 6.0 |
| 6 | PEG-400 | | | q.s to 100 | |

The pre-concentrate of docetaxel according to formula given in Table 25 was prepared using polyvinyl pyrrolidone of different molecular weights.

It was found that the increased molecular weight of polyvinyl pyrrolidone improved the stability of the nanodipsersion in terms of aggregation and the time during which the nano-dipsersion remained stable.

EXAMPLE 23 and COMPARATIVE EXAMPLES IV, V and VI

TABLE 26

| | | Quantity (% w/v) | | | |
|---|---|---|---|---|---|
| Sr. No. | Ingredients | EXAMPLE 23 | COMPARATIVE | | |
| | | | IV | V | VI |
| 1 | Docetaxel | 6 | 6 | 6 | 6 |
| 2 | Cholesteryl sulphate sodium | 0.4 | 0.8 | 0.4 | 5 |
| 3 | Caprylic acid | 0.4 | — | — | — |
| 4 | Polyvinyl pyrroliodone (k17) | 5 | 5 | 5 | 10.6 |
| 5 | Ethanol | 6 | 6 | 6 | 6 |
| 6 | PEG-400 | q.s | q.s | q.s | q.s |
| 7 | Dextrose (5% w/v) | To achieve 0.5 mg/ml | | | |

Specified amounts of drug, cholesteryl sulphate and caprylic acid were weighed accurately in a glass vessel.

Contents were dissolved in the required quantity of absolute ethanol and PEG-400 with stirring and by heating at 45° C. to obtain a concentrated drug solution.

The solution was filtered through 0.2μ PVDF membrane filter.

Dextrose solution (5% w/v) was prepared and was slowly added to the vial containing the concentrated drug solution (30 mg), followed by the addition of remaining 5% w/v dextrose solution with gentle shaking to get a transluscent nanodispersion at the dilution of 1.5 mg/ml.

pH of the nanodispersion was checked by using pH Meter (Mettler Toledo-seven easy).

Particle size of the nanodispersion was checked by Particle size analyzer (Nano-ZS, Malvern.

TABLE 27

| | Observations | | | |
|---|---|---|---|---|
| Parameters evaluated | Example 23 | Comparative | | |
| | | IV | V | VI |
| pH | 4.00 | 4.0 | | |
| Zeta Potential | −26.0 mV | −30.4 mV to −34.2 mV | | |
| Appearance | Transparent, bluish tint | | | |
| Particle Size (nm) | | | | |
| Initial | 114 | 174 | 171 | 364 |
| 1 hours | 114 | 164 | Whitish Hazy | |
| 2 hours | 113 | Whitish Hazy | | |
| 3 Hours | 129 | | | |
| 4 hours | Change in appearance | | | |

EXAMPLE 24

TABLE 28

| Sr. No. | Ingredients | Quantity (% w/v) |
|---|---|---|
| 1 | Docetaxel | 9 |
| 2 | Cholesteryl sulfate sodium | 0.6 |
| 3 | Caprylic acid | 0.6 |
| 4 | Polyvinylpyrrolidone (PVP) K-17 | 5 |
| 5 | Ethanol | 9 |
| 6 | Polyethylene glycol 400 | q.s |

Specified amounts of docetaxel, sodium cholsteryl sulphate, caprylic acid and polyvinyl pyrrolidone were weighed in a vial. The dehydrated amount of alcohol and polyethylene glycol were mixed and dissolved in a bath sonicator at slightly warming at 40° C., until a clear transparent pre-concentrate is obtained. The preconcentrate was diluted with the aqueous vehicle containing different additives as given in table 29. The so formed nanodispersion was subjected to mean particle size measurement using Malvern particle size analyzer.

TABLE 29

Effect of additives in the aqueous vehicle on stability of the nanodispersion

| | Example 24 | | | |
|---|---|---|---|---|
| | A | B | C | D |
| Diluent | 0.01% Arginine in 5% Dextrose Injection USP | 1% Histidine in 5% Dextrose Injection USP | 1% Histidine + 0.001% Disodium edetate in 5% Dextrose Injection | 0.5% Histidine + 0.001% Disodium edetate in 5% Dextrose Injection |
| Strength: | 0.5 mg/ml | 0.5 mg/ml | 0.5 mg/ml | 0.5 mg/ml |
| Description of Nanodispersion | Almost Transparent, Bluish tint | Almost Transparent, Bluish tint | Almost Transparent, Bluish tint | Almost Transparent, Bluish tint |
| Physical stability Particle Size: | | | | |
| 0 h | 143 nm, | 130 | 128 nm | 118 nm, |
| 1 h | 146 nm, | 133 | 131 nm | 121 nm, |
| 3 h | 147 nm, | 136 nm, | 131 nm | 123 nm |
| 5 h | — | 138 nm, | — | 130 nm, |
| 6 h | — | — | 135 nm | — |
| 8 h | 145 nm, | — | — | 136 nm, |
| Zeta Potential | −52.2 mV | −32.0 mV | −29.0 mv | −29.8 mV |
| pH | 8.11 | 7.06 | 7.2 | 6.74 |
| Remarks | Stable for 8 h | Stable for 5 h | Stable for 6 h | Stable for 8 h |
| Assay Chemical stability | — | — | — | |
| Initial | | | | 103.57 |
| 25° C./60% RH | | | | |
| 1 Month | | | | 100.37 |
| Fridge 2-8° C. | | | | |
| 1 Month | | | | 99.02 |
| 40° C./75% RH | | | | |
| 1 Month | | | | 101.53 |

Results of the particle size distribution of the example in which 0.5% Histidine, 0.001% Disodium edetate in 5% Dextrose Injection are represented in FIG. 5 (*a*) and FIG. 5 (*b*). FIG. 5 (*a*) shows a histogram showing particle size distribution of the nanodispersion at initial time (average particle size=98 nms and FIG. 5 (*b*)) shows a histogram showing particle size distribution of the nanodispersion at 8 hours with a mean particle size =96.4 nms indicating a stable nature of the nanodispersion.

EXAMPLE 25

Acute Toxicity of Paclitaxel Nanodispersion of the Present Invention in CD-1 Mice Test Items:
1. Compositions of example 12a were used upon dilution with dextrose 5% w/v to 10 mg/ml along with placebo
2. Compositions of example 9 were used upon dilution with dextrose 5% w/v to 8 mg/ml along with placebo and
3. ABRAXANE® diluted with 0.9% sodium chloride to 10 mg/ml.

CD-1 mice were acclimatized to the conditions of individually ventilated cage system (IVC) in animal quarter number 2, for 5 days. After veterinary health check, 5 male and 5 female mice were allocated to each dose group. Mice had free access to water and feed throughout the experimental period. Test items and placebos of the below doses were administered intravenously, as such without any dilution with any vehicle, through caudal tail vein of mice using 26 gauge needle attached to a graduated syringe. Before injection, tail was swabbed with warm water to dilate the blood vessels. A total dose of 150, 200, 250, 300, 350 and 400 mg/kg were tested for Paclitaxel nanodispersion (Example 12), doses of 250, 300 and 400 mg/kg were tested for placebo (Placebo of example 12), doses of 200 and 250 mg/kg were tested for Paclitaxel nanodispersion (Example 9), dose of 250 mg/kg was tested for placebo (Placebo of example 9), and dose of 300 mg/kg was tested for ABRAXANE®. All these formulations were administered intravenously to CD-1 mice via. 3 divided doses with a gap of one hour between two doses/injections. After last injection animals were observed twice daily for 1 hour and between 4-6 hours post dosing. Thereafter, mice were observed twice daily to record toxic symptoms and mortality, if any, upto day 45.

TABLE 30

| Test item | Dose of Paclitaxel i.v. (mg/kg) | % Mortality | $LD_{50}$ |
|---|---|---|---|
| Paclitaxel Nanodispersion (of Example 12a) | 150 | 0 | ~342.5 mg/kg |
|  | 200 | 0 |  |
|  | 250 | 0 |  |
|  | 300 | 0 |  |
|  | 350 | 60 |  |
|  | 400 | 90 |  |
| Placebo of Example 12a | 250 | 0 |  |
|  | 300 | 0 |  |
|  | 400 | 0 |  |
| Paclitaxel Nanodispersion (of Example 9) | 200 | 20 | >250 mg/kg |
|  | 250 | 20 |  |
| Placebo of Example 9 | 250 | 0 |  |
| ABRAXANE ® | 300 | 90 |  |

The results indicated that Paclitaxel nanodispersion of example 12 showed 90% mortality at 400 mg/kg and zero percent mortality at dose of 300 mg/kg. No mortality observed with the placebo of example 12 at the highest dose tested (400 mg/kg). On linear extrapolation of Paclitaxel nanodispersion, the $LD_{50}$ and LIN, values obtained were 342.5 mg/kg and 310 mg/kg respectively Similarly, Paclitaxel nanodispersion of example 9 showed 20% mortality at 250 mg/kg and $LD_{50}$ for paclitaxel nanodispersion was >250 mg/kg. No mortality observed with the placebo of example 9 at the highest dose tested (250 mg/kg). The marketed nanoparticle formulation, ABRAXANE® showed toxicity of 90% at 300 mg/kg. These data clearly shows that nanodispersion composition of the present invention may be less toxic as compared to the marketed ABRAXANE® Also, on comparison of $LD_{50}$ value of nanodispersion composition of the present invention (342.5 mg/kg) with the $LD_{50}$ value of marketed TAXOL formulation (7.5-12.0 mg/Kg; U.S. Pat. No.- 6,753,006), it is evident that the $LD_{50}$ value observed for Paclitaxel nanodispersion of the present invention is much greater than the $LD_{50}$ value of marketed TAXOL solution.

Acute Toxicity of Paclitaxel Nanodispersion of the Present Invention in SD Rats

Test Items:

1. Composition of example 9 were used upon dilution with dextrose 5% w/v to 10 mg/ml along with placebo, and
2. ABRAXANE®diluted with 0.9% sodium chloride to 5 mg/ml.

Rats were acclimatized to the conditions of individually ventilated cage system (IVC) in animal quarter number 3 for 5 days. After veterinary health check, 5 male and 5 female SD rats were allocated to each dose group. Rats had free access to water and feed throughout the experimental period. Test items and placebos of the below doses were administered intravenously, as such without any dilution with any vehicle, through caudal tail vein of rat using 26 gauge needle attached to a graduated syringe. Before injection, tail was swabbed with warm water to dilate the blood vessels. After injection animals were observed twice daily for 1 hour and between 4-6 hours post dosing. Thereafter, rats were observed twice daily to record toxic symptoms and mortality, if any, upto day 14.

TABLE 31

Acute Toxicity Studies in SD rats

| Test Item | Dose of Paclitaxel i.v. (mg/kg) | % Mortality |
|---|---|---|
| Paclitaxel nanodispersion (Example 9) | 60 | 30 |
|  | 90 | 40 |
| Placebo of example 9 | 90 | 0 |
|  | $LD_{50}$ in SD rats: >90/mg/kg |  |
| ABRAXANE ® | 70 | 100 |

The results indicate that Paclitaxel nanodispersion of the present invention of example 9 showed 40% mortality at 90 mg/kg. No mortality observed with the placebo of example 9 at the highest dose tested (90 mg/kg). The $LD_{50}$ for paclitaxel nanodispersion of the present invention was >90 mg/kg. The marketed nanoparticle formulation, ABRAXANE® showed toxicity of 100% at 70 mg/kg.

The results clearly indicate that nanodispersion composition of the present invention minimizes the toxicity associated with the drug and broadens the effective administrable therapeutic range of the drug and are less toxic than the existing marketed formulations such as ABRAXANE®.

EXAMPLE 26

Composition of example 24B were used upon dilution with dextrose 5% w/v to 10 mg/ml along with placebo and the marketed formulation Taxotere® diluted to 10 mg/ml were subjected to acute Toxicity Study of Docetaxel Nanodispersion and Placebo in CD-1 Mice by Intravenous Route. Mice were acclimatized to the conditions of experimental room in animal quarter number 2 for 6 days. After veterinary health check, 5 male and 5 female mice were allocated randomly to each dose group. Mice had free access to water and feed throughout the study period. Test item and placebo were administered intravenously as such without dilution with any vehicle, through caudal tail vein of mice using 26 gauge needle attached to a graduated syringe. Before injection, tail was swabbed with warm water to dilate the blood vessel. A total dose of 200, 250 and 300 mg/kg were tested for Docetaxel nanodispersion (Example 24B), Placebo at the highest dose (Placebo of example 24B). These formulations were administered intravenously to CD-1 mice via. 3 divided doses with a gap of one hour between two doses/injections. After last injection, animals were observed for 1 h and between 4-6 h of post-dosing. Thereafter, mice were observed twice daily for clinical symptoms and mortality for 15 days. Body weights of all surviving animals were recorded on days 1, 7 and 14 post-dosing. On day 15, necropsy of surviving animals was performed and gross pathology, if any, was recorded.

TABLE 32

Results of the acute Toxicity Study

| Test item | Dose of docetaxel i.v. (mg/kg) | % Mortality | $LD_{10}$ |
|---|---|---|---|
| Docetaxel Nanodispersion (of Example 24B) | 200 | 0 |  |
|  | 250 | 0 |  |
|  | 300 | 10 | 300 mg/kg |
| Placebo of Example-24 B | 300 | 0 |  |
| Taxotere ® | 80 | 0 |  |
|  | 120 | 10 | $LD_{10}$: 120 mg/kg |
|  | 160 | 70 | $LD_{50}$: 150 mg/kg |

The results indicated that Docetaxel nanodispersion of the present invention of example-24B showed 10% mortality at 300 mg/kg and $LD_0$ at dose of 250 mg/kg. No mortality observed with the placebo at the highest dose tested (300 mg/kg). The marketed formulation, Taxotere® showed toxicity of 10% at 120 mg/kg. It is evident that the $LD_{10}$ value observed for Docetaxel nanodispersion of the present invention is much greater than the $LD_{10}$ value of marketed Taxotere® solution formulation. The reported $LD_{10}$ value of Taxotere® is 95 mg/kg (Ref: SBA-NDA-20449).

EXAMPLE 27

Antitumor efficacy (tumor regression) of paclitaxel nanodispersion (of composition of Example 12a) in nude mice implanted with MX-1 tumor xenografts.

Animals: Species: Mice, Strain: Balb/c nude, Sex: Female, Age: 6-8 weeks (18.9 g±1.8 gs)
Human Tumor Xenografts: MX-1 (breast)
Test sample: Composition of Example 12a, diluted with dextrose 5% to 2 mg/ml.
Reference: Marketed formulation, ABRAXANE®, reconstituted to 2 mg/ml with 0.9% sodium chloride.
Placebo: test sample without the taxane derivative.
Dose: 20 mg/kg, once daily for 5 consecutive days, intravenous route of administration, 10 ml/kg body wt.
Study Design:
1. Tumor was implanted by subcutaneous route on the right flank of the animal as 30 mg to 40 mg fragments.
2. The tumor was allowed to increase to a median size of 125 mm3 to 132 mm3 before initiation of treatment.
3. The tumor bearing animals were divided in groups consisting of ten animals.
4. The animals were administered doses as described above and tumor was evaluated as below.

Results: Significant reduction in tumor volume was seen in Test from day 8 onwards as compared to control group. Tumors were evaluated in tumor Volume (mm3) with respect to time in days. The data for 42 days is represented graphically in FIG. 1.

Moderate antitumor activity was seen in reference at 20 mg/kg (optimal % T/C<20), whereas highly significant antitumor activity was seen in Test at 20 mg/kg body weight (optimal % T/C<10). Optimal % T/C value for Test and Reference was 0 and 13.34 respectively. Highly significant antitumor activity was demonstrated by test (Paclitaxel Nanodispersion Concentrate for injection) at 20 mg/kg in MX-1 human mammary carcinoma xenografts in nude mice.

EXAMPLE 28

Antitumor Efficacy (Tumor Regression) of Paclitaxel Nanodispersion (of Composition of Example 9) in Nude Mice Implanted with MX-1 Tumor Xenografts Animals: Species: Mice, Strain: Athymic nude, Sex: Female, Age: 6-8 weeks (20-25 g)
Human Tumor Xenografts: MX-1 (breast)
Test sample: Composition of Example 9, diluted with dextrose 5% to 2 mg/ml.
Reference: Marketed formulation, ABRAXANE® diluted with 0.9% w/v sodium chloride to 2 mg/ml.
Dose: 20 mg/kg, once daily for 5 consecutive days, i.v., 10 ml/kg body wt.
Study Design:
1. Tumor was implanted by subcutaneous route on the right flank of the animal as approximately 2×2 mm fragments.
2. The tumor was allowed to increase to a size of 200 mm$^3$ to 220 mm$^3$ before initiation of treatment.
3. The tumor bearing animals were divided in groups consisting of ten animals.
4. The animals were administered doses as described above and tumor was evaluated as below.

Figure 2:
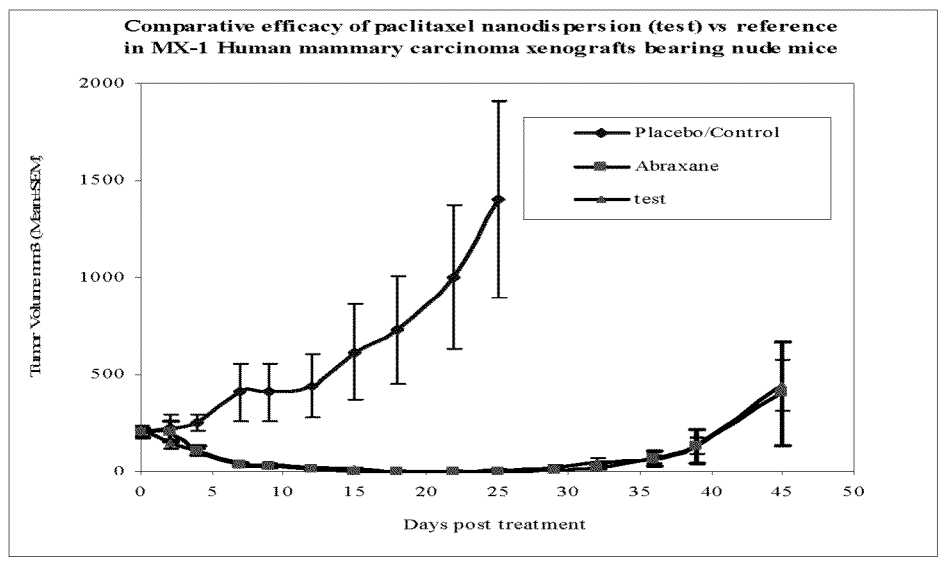
FIG. 2: It represents a comparative account of change in tumor volume with time (in days) of human breast tumor xenograft (MX-1) implanted in Athymic female nude mice for control sample, reference sample (ABRAXANE®) and test sample (Composition of example 9 of the present invention) as per the study detailed in Example 28.

Tumor Evaluation: Tumors were evaluated in tumor Volume (mm3) with respect to time in days. The data for 42 days is represented graphically in FIG. 2.

Results: Highly significant antitumor activity is seen in test and Abraxane® groups (optimal % T/C<10). Optimal % T/C value for test and Abraxane® at 20 mg/kg dose was 0.25 and 0.00 respectively. No significant decrease in body weight was observed in Placebo/Control group as compared to day 0. Highly significant antitumor activity was demonstrated by test (Paclitaxel Nanodispersion Concentrate for injection) at 20 mg/kg in MX-1 human mammary carcinoma xenografts in nude mice.

EXAMPLE 29

Antitumor Efficacy (Tumor Regression) of Paclitaxel Nanodispersion (of Composition of Example 9) in Nude Mice Implanted with HT-29 Human Colon Tumor Xenografts Animals: Species: Mice, Strain: Athymic nude, Sex: male, Age: 6-8 weeks (20-25 g)
Human Tumor Xenografts: HT-29 Human Colon.
Test sample: Composition of Example 9, diluted with dextrose 5% to 2 mg/ml.
Dose: 20 mg/kg, once daily for 5 consecutive days, i.v., 10 ml/kg body wt.
Reference:
(a) Marketed Formulation, Abraxane® Diluted to 2 Mg/ml Reconstituted to 2 Mg/mMl with 0.9% Sodium chloride.
Dose: 20 mg/kg, once daily for 5 consecutive days, i.v., 10 ml/kg body wt.
(b) Marketed formulation, ONCOTAXEL®.
Dose: 13.4 mg/kg once daily for 5 consecutive days, i.v.
Study Design:
1. Tumor was implanted by subcutaneous route on the right flank of the animal as approximately 2×2×2 mm fragments.
2. The tumor was allowed to increase to a size of 130 mm3 to 160 mm3 before initiation of treatment.
3. The tumor bearing animals were divided in groups consisting of ten animals.
4. The animals were administered doses as described above and tumor was evaluated as below.

Figure 3:
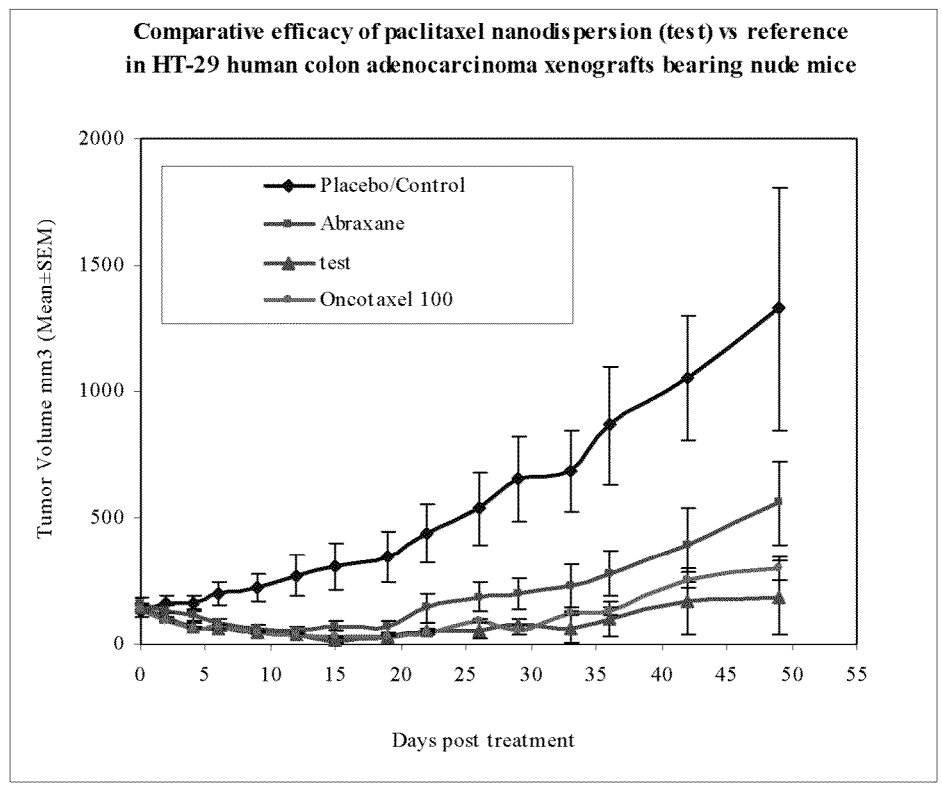
FIG. 3: It represents a comparative account of change in tumor volume with time (in days) of human colon tumor xenograft (HT-29) implanted in Athymic male nude mice for control sample, test sample (Composition of example 9 of the present invention) and two reference samples (ABRAXANE® and ONCOTAXEL®) as per the study detailed in Example 29.

Tumor Evaluation: Tumors are evaluated for reduction in tumor volume (mm3) with respect to time in days. The data for 49 days represented in FIG. 3.

Results: Highly significant antitumor activity is seen in test and Oncotaxel® 100 groups (optimal % T/C<10). Optimal % T/C value for the test at 20 mg/kg and Oncotaxel® 100 at 13.4 mg/kg dose was 5.92 and 8.79 respectively, whereas moderate antitumor activity is shown by Abraxane® with an optimal % T/C value of 20.33. Highly significant anti tumor activity was demonstrated by test (Paclitaxel Nanodispersion Concentrate for injection) at 20 mg/kg in HT-29 human Colon carcinoma xenografts in nude mice.

We claim:

1. A solution consisting of
   (a) a taxane derivative selected from paclitaxel or docetaxel
   (b) a polymer selected from the group consisting of polyvinylpyrrolidone, polyglutamic acid or its salts and hyaluronic acid or its salts,
   (c) a surfactant consisting of a mixture of caprylic acid or its salts and cholesteryl sulphate or its salts, and
   (d) a water miscible solvent selected from the group consisting of alcohol, polyethylene glycol and polypropylene glycol,
   such that dilution of the solution with an aqueous liquid vehicle or vice versa, with agitation or shaking results in the formation of a nanodispersion that remains stable for at least 4 hours with no aggregation or crystallization of the taxane derivative, and wherein the nanodispersion is administered to a patient by intravenous infusion.

2. The solution as claimed in claim 1, wherein the weight ratio of the surfactant to the taxane derivative is in the range of about 1:5 to 1:10.

3. The solution as claimed in claim 1, wherein the weight ratio of the surfactant to the taxane derivative is about 1:6.

4. The solution as claimed in claim 1, wherein the polymer is polyvinylpyrrolidone having a molecular weight in the range of about 1000 to about 50,000, and present in an amount ranging from 0.001% w/v to 10% w/v.

5. The solution as claimed in claim 1, wherein the aqueous liquid vehicle comprises about 5% w/v to about 10% w/v dextrose solution.

6. The solution as claimed in claim 5, wherein the nanodispersion formed upon dilution of the solution with an aqueous liquid vehicle comprises caprylic acid in an amount ranging from about 0.01% w/v to about 0.5% w/v.

7. The solution as claimed in claim 5, wherein the nanodispersion formed upon dilution of the solution with an aqueous liquid vehicle comprises cholesteryl sulphate in an amount ranging from about 0.01% w/v to about 0.5% w/v.

8. The solution as claimed in claim 5, wherein the nanodispersion formed upon dilution of the solution with an aqueous liquid vehicle comprises ethanol in an amount ranging from about 0.001% w/v to about 5% w/v and polyethylene glycol in an amount ranging from about 0.05% w/v to about 5.0% w/v.

9. A kit comprising two containers, wherein
   a first container comprises a solution consisting of:
      (a) a taxane derivative selected from paclitaxel or docetaxel,
      (b) a polymer selected from the group consisting of polyvinylpyrrolidone, polyglutamic acid or its salts and hyaluronic acid or its salts,
      (c) a surfactant consisting of a mixture of caprylic acid or its salts and cholesteryl sulphate or its salts, and
      (d) a water miscible solvent selected from the group consisting of alcohol, polyethylene glycol and polypropylene glycol; and
   a second container comprises an aqueous liquid vehicle;
   such that addition of the contents of the first container to the second container and vice versa with agitation or shaking results in the formation of a nanodispersion that remains stable for at least 4 hours with no aggregation or crystallization of the taxane derivative.

10. A nanodispersion of a taxane derivative that remains stable for at least 4 hours with no aggregation or crystallization of the taxane derivative, wherein the nanodispersion is formed by addition of an aqueous liquid vehicle to a solution consisting of:
   (a) the taxane derivative selected from paclitaxel or docetaxel,
   (b) a polymer selected from the group consisting of polyvinylpyrrolidone, polyglutamic acid or its salts and hyaluronic acid or its salts,
   (c) a surfactant consisting of a mixture of caprylic acid or its salts and cholesteryl sulphate or its salts, and
   (d) a water miscible solvent selected from the group consisting of alcohol, polyethylene glycol and polypropylene glycol;
   or vice versa, with agitation or shaking.

* * * * *